(12) United States Patent
Renzi

(10) Patent No.: US 7,629,324 B2
(45) Date of Patent: *Dec. 8, 2009

(54) ANTISENSE OLIGONUCLEOTIDES FOR TREATING ATOPIC DISEASES AND NEOPLASTIC CELL PROLIFERATION

(75) Inventor: Paolo Renzi, Westmount (CA)

(73) Assignee: Topigen Pharmaceutiques Inc. (CA)

( * ) Notice: Subject to any disclaimer, the term of this patent is extended or adjusted under 35 U.S.C. 154(b) by 502 days.

This patent is subject to a terminal disclaimer.

(21) Appl. No.: 10/958,204

(22) Filed: Oct. 4, 2004

(65) Prior Publication Data

US 2005/0282762 A1 Dec. 22, 2005

Related U.S. Application Data

(63) Continuation of application No. 09/719,737, filed as application No. PCT/CA99/00572 on Jun. 17, 1999, now Pat. No. 6,822,087.

(51) Int. Cl.
*C07H 21/02* (2006.01)
*C07H 21/04* (2006.01)
*C12Q 1/68* (2006.01)
*C12P 19/34* (2006.01)
*C12N 5/00* (2006.01)

(52) U.S. Cl. .................. 514/44; 536/23.1; 536/24.3; 536/24.33; 536/24.5

(58) Field of Classification Search .............. 536/23.1, 536/24.3, 24.33, 24.5
See application file for complete search history.

(56) References Cited

U.S. PATENT DOCUMENTS 6,822,087 B1 * 11/2004 Renzi ........................ 536/24.5

FOREIGN PATENT DOCUMENTS

| WO | 9622371 | 7/1996 |
|----|---------|--------|
| WO | 9632481 | 10/1996 |
| WO | 9636291 | 11/1996 |
| WO | 9720926 | 6/1997 |
| WO | 9722698 | 6/1997 |
| WO | 9702344 | 7/1997 |
| WO | 9728190 | 8/1997 |
| WO | 9741154 | 11/1997 |
| WO | 9741225 | 11/1997 |
| WO | 9913886 | 3/1999 |

OTHER PUBLICATIONS

Allakhverdi et al. (American Journal of Respiratory and Critical Care Medicine, 2002 vol. 165:1015-1021).*
Allakhverdi et al. (Annals of the New York Academy of Sciences, 2006 vol. 1082:62-73).*
Fortin et al. (Oligonucleotides, 2006 vol. 16:203-212).*
Jubinsky, Paul T. et al., Blood, 90(5):1867-1873 (1997). "The Beta-Chain of the Interleukin-3 Receptor Functionally Associates With the Erythropoietin Receptor."

(Continued)

Primary Examiner—Sean McGarry
Assistant Examiner—Terra Cotta Gibbs
(74) Attorney, Agent, or Firm—Nixon Peabody LLP

(57) ABSTRACT

The present invention relates to the use of antisense oligonucleotides directed against specific nucleic acid sequences coding for receptors, alone or in combination, in order to inhibit the inflammatory reaction that is present in asthma, atopy or hypereosinophilia and to inhibit neoplastic cell proliferation. The antisense oligonucleotides of the present invention are used for treating and/or preventing asthma, allergy, hypereosinophilia, general inflammation or cancer. The oligonucleotides of the present invention are more specifically directed against nucleic acid sequences coding for a CCR3 receptor, a common sub-unit of IL-4 and IL-13 receptors, or a common sub-unit of IL-3, IL-5 and GM-CSF receptors.

12 Claims, 29 Drawing Sheets

OTHER PUBLICATIONS

Devos R, et al., "Interleukin-5 and its receptor: a drug target for eosinophilia associated with chronic allergic disease." J Leukoc Biol 57(6):813-9, 1995.

Green DW, et al., "Antisense oligonucleotides: an evolving technology for the modulation of gene expression in human disease." J Am Coll Surg 191(1):93-105, 2000.

Jen KY and Gewirtz AM, "Suppression of gene expression by targeted disruption of messenger RNA: available options and current strategies." Stem Cells 18(5):307-19, 2000.

Branch AD, "A good antisense molecule is hard to find." Trends Biochem Sci 23(2):45-50, 1998.

Agrawal S and Kandimalla ER, "Antisense therapeutics: is it as simple as complementary base recognition?" Mol Med Today 6(2):72-81, 2000.

Ponath PD, et al., "Molecular cloning and characterization of a human eotaxin receptor expressed selectively on eosinophils." J Exp Med 183(6):2437-48, 1996.

Ikizawa K, et al., "Inhibition of IL-4 receptor up-regulation on B cells by antisense oligodeoxynucleotide suppresses IL-4-induced human IgE production." Clin Exp Immunol 100(3):383-9, 1995.

Hayashida K et al., "Molecular cloning of a second subunit of the receptor for human granulocyte-macrophage colony-stimulating factor (GM-CSF): reconstitution of a high-affinity GM-CSF receptor." Proc Natl Acad Sci U S A 87 (24):9655-9, 1990.

* cited by examiner

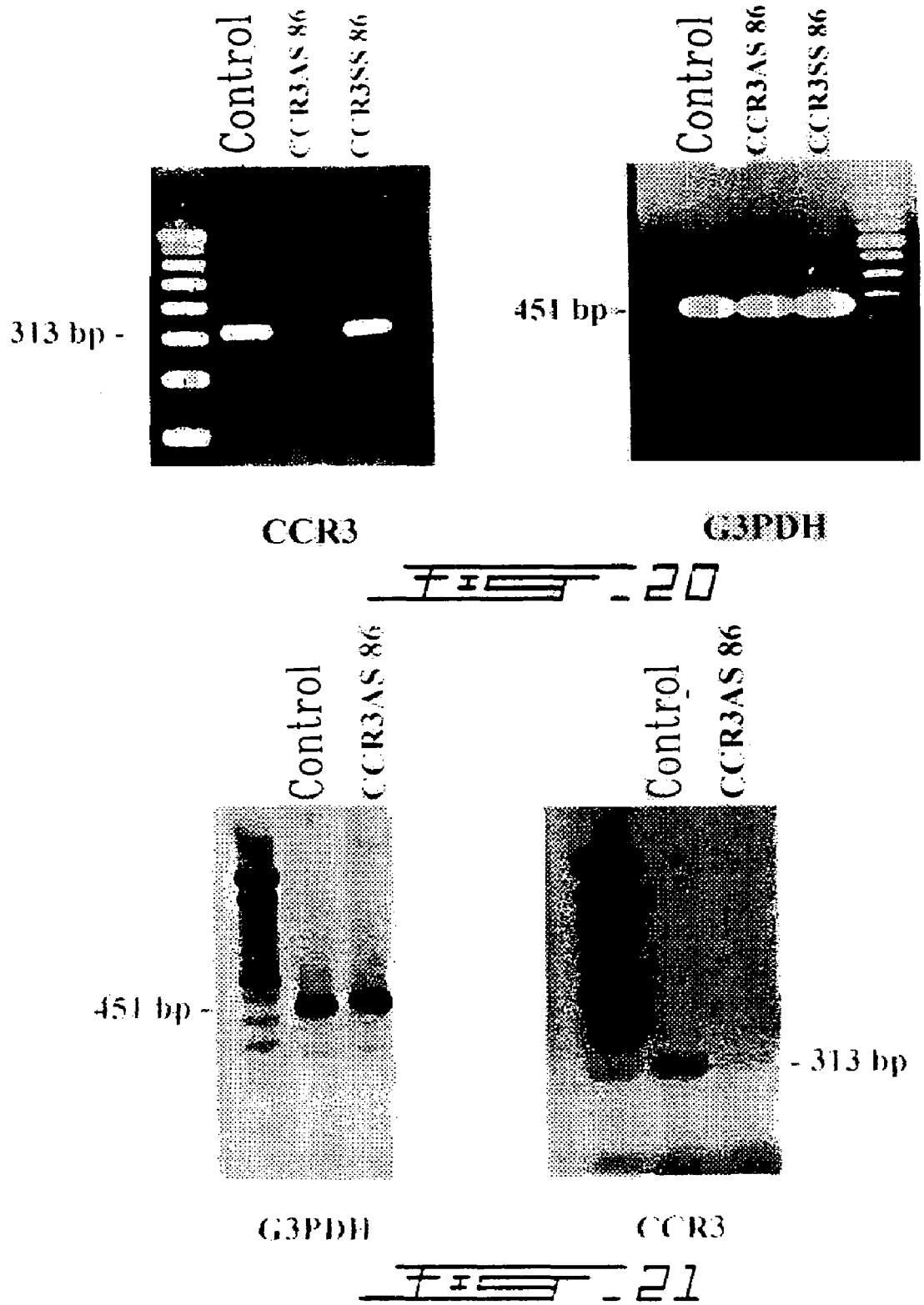

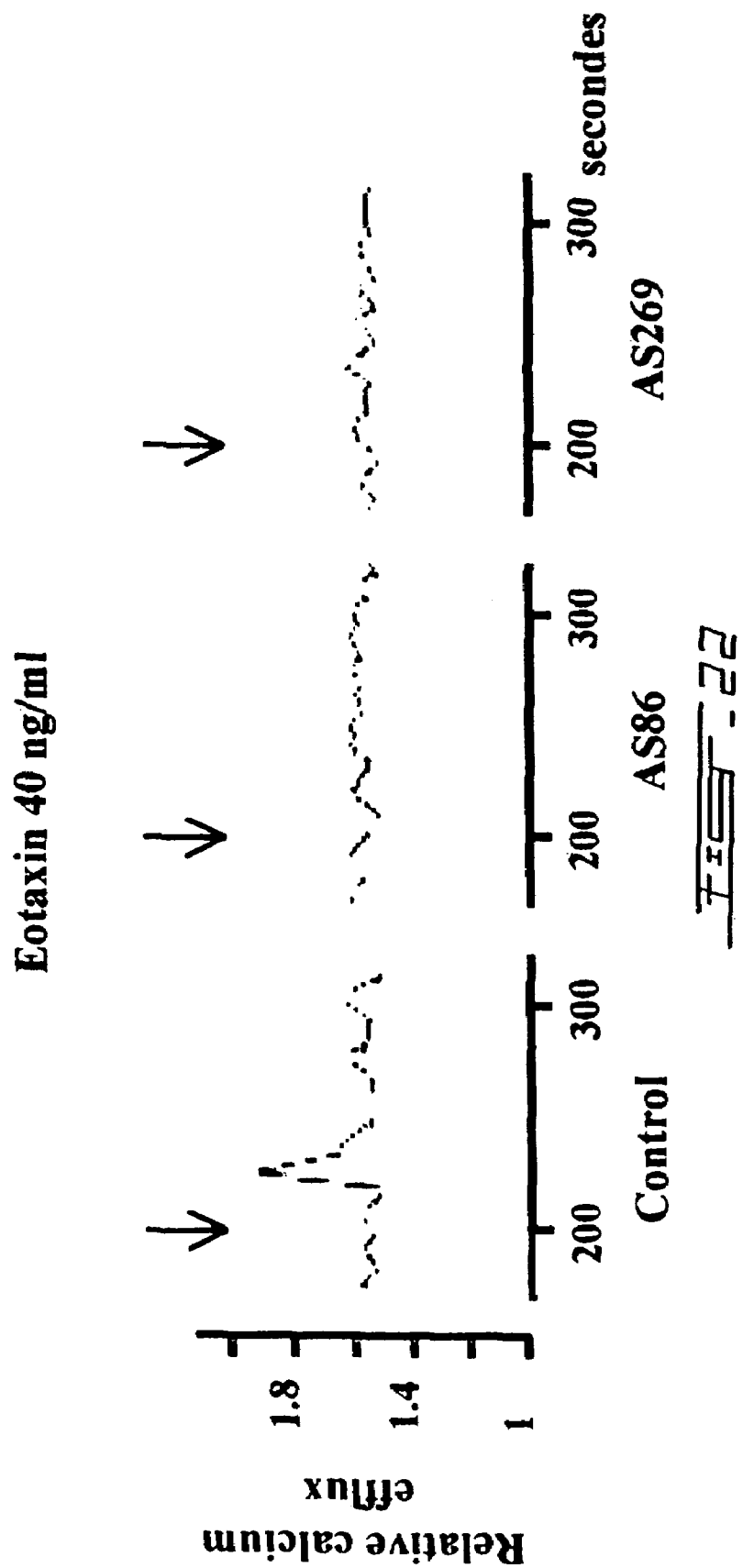

US 7,629,324 B2

```
                         SEQUENCE LISTING

<160> NUMBER OF SEQ ID NOS: 23

<210> SEQ ID NO 1
<211> LENGTH: 20
<212> TYPE: DNA
<213> ORGANISM: Artificial Sequence
<220> FEATURE:
<223> OTHER INFORMATION: Antisense oligonucleotide inhibiting the common
      subunit of IL-4 and IL-13 human receptor

<400> SEQUENCE: 1
agaccttcat gttcccagag                                              20

<210> SEQ ID NO 2
<211> LENGTH: 20
<212> TYPE: DNA
<213> ORGANISM: Artificial Sequence
<220> FEATURE:
<223> OTHER INFORMATION: Antisense oligonucleotide inhibiting the common
      subunit of IL-4 and IL-13 human receptor

<400> SEQUENCE: 2
gttcccagag cttgccacct                                              20

<210> SEQ ID NO 3
<211> LENGTH: 19
<212> TYPE: DNA
<213> ORGANISM: Artificial Sequence
<220> FEATURE:
<223> OTHER INFORMATION: Antisense oligonucleotide inhibiting the common
      subunit of IL-4 and IL-13 human receptor

<400> SEQUENCE: 3
cctgcaagac cttcatgtt                                               19

<210> SEQ ID NO 4
<211> LENGTH: 20
<212> TYPE: DNA
<213> ORGANISM: Artificial Sequence
<220> FEATURE:
<223> OTHER INFORMATION: Antisense oligonucleotide inhibiting the common
      subunit of IL-4 and IL-13 human receptor

<400> SEQUENCE: 4
cgcccacagc ccgcagagcc                                              20

<210> SEQ ID NO 5
<211> LENGTH: 20
<212> TYPE: DNA
<213> ORGANISM: Artificial Sequence
<220> FEATURE:
<223> OTHER INFORMATION: Antisense oligonucleotide inhibiting the common
      subunit of IL-4 and IL-13 human receptor

<400> SEQUENCE: 5
ctccatgcag cctctcgcct                                              20
```

```
<210> SEQ ID NO 6
<211> LENGTH: 20
<212> TYPE: DNA
<213> ORGANISM: Artificial Sequence
<220> FEATURE:
<223> OTHER INFORMATION: Antisense oligonucleotide inhibiting the common
      subunit of IL-4 and IL-13 human receptor

<400> SEQUENCE: 6
ccgccggcgc agagcagcag                                                   20

<210> SEQ ID NO 7
<211> LENGTH: 20
<212> TYPE: DNA
<213> ORGANISM: Artificial Sequence
<220> FEATURE:
<223> OTHER INFORMATION: Antisense oligonucleotide inhibiting the common
      subunit of IL-4 and IL-13 human receptor

<400> SEQUENCE: 7
cgcccccgcc cccgccccg                                                    20

<210> SEQ ID NO 8
<211> LENGTH: 19
<212> TYPE: DNA
<213> ORGANISM: Artificial Sequence
<220> FEATURE:
<223> OTHER INFORMATION: Sense oligonucleotide for IL-3, IL-5 and GM-CSF

<400> SEQUENCE: 8
accatcccgc tgcagaccc                                                    19

<210> SEQ ID NO 9
<211> LENGTH: 19
<212> TYPE: DNA
<213> ORGANISM: Artificial Sequence
<220> FEATURE:
<223> OTHER INFORMATION: Antisense oligonucleotide inhibiting the common
      subunit of IL-3, IL-5 and GM-CSF human receptor

<400> SEQUENCE: 9
gggtctgcag cgggatggt                                                    19

<210> SEQ ID NO 10
<211> LENGTH: 19
<212> TYPE: DNA
<213> ORGANISM: Artificial Sequence
<220> FEATURE:
<223> OTHER INFORMATION: Antisense oligonucleotide inhibiting the common
      subunit of IL-3, IL-5 and GM-CSF human receptor

<400> SEQUENCE: 10
ggtctgcagc gggatggtt                                                    19

<210> SEQ ID NO 11
<211> LENGTH: 19
<212> TYPE: DNA
<213> ORGANISM: Artificial Sequence
<220> FEATURE:
<223> OTHER INFORMATION: Antisense oligonucleotide inhibiting the common
      subunit of IL-3, IL-5 and GM-CSF human receptor

<400> SEQUENCE: 11
agggtctgca gcgggatgg                                                    19
```

```
<210> SEQ ID NO 12
<211> LENGTH: 19
<212> TYPE: DNA
<213> ORGANISM: Artificial Sequence
<220> FEATURE:
<223> OTHER INFORMATION: Antisense oligonucleotide inhibiting the common
      subunit of IL-3, IL-5 and GM-CSF human receptor

<400> SEQUENCE: 12
gcagggtctg cagcgggat                                                19

<210> SEQ ID NO 13
<211> LENGTH: 19
<212> TYPE: DNA
<213> ORGANISM: Artificial Sequence
<220> FEATURE:
<223> OTHER INFORMATION: Antisense oligonucleotide inhibiting the common
      subunit of IL-3, IL-5 and GM-CSF human receptor

<400> SEQUENCE: 13
gcagcgggat ggtttcttc                                                19

<210> SEQ ID NO 14
<211> LENGTH: 19
<212> TYPE: DNA
<213> ORGANISM: Artificial Sequence
<220> FEATURE:
<223> OTHER INFORMATION: Antisense oligonucleotide inhibiting the common
      subunit of IL-3, IL-5 and GM-CSF human receptor

<400> SEQUENCE: 14
cagcgggatg gtttcttct                                                19

<210> SEQ ID NO 15
<211> LENGTH: 19
<212> TYPE: DNA
<213> ORGANISM: Artificial Sequence
<220> FEATURE:
<223> OTHER INFORMATION: Antisense oligonucleotide inhibiting the common
      subunit of IL-3, IL-5 and GM-CSF human receptor

<400> SEQUENCE: 15
gtctgcagcg ggatggttt                                                19

<210> SEQ ID NO 16
<211> LENGTH: 18
<212> TYPE: DNA
<213> ORGANISM: Artificial Sequence
<220> FEATURE:
<223> OTHER INFORMATION: Antisense oligonucleotide inhibiting the common
      subunit of IL-3, IL-5 and GM-CSF rat receptor

<400> SEQUENCE: 16
tggcacttta ggtggctg                                                 18

<210> SEQ ID NO 17
<211> LENGTH: 18
<212> TYPE: DNA
<213> ORGANISM: Artificial Sequence
<220> FEATURE:
<223> OTHER INFORMATION: Sense oligonucleotide for the common subunit of
      IL-3, IL-5 and GM-CSF rat receptor

<400> SEQUENCE: 17
cagccaccta aagtgcca                                                 18
```

```
<210> SEQ ID NO 18
<211> LENGTH: 19
<212> TYPE: DNA
<213> ORGANISM: Artificial Sequence
<220> FEATURE:
<223> OTHER INFORMATION: Antisense oligonucleotide inhibiting the CCR3
      human receptor

<400> SEQUENCE: 18
ctgggccatc agtgctctg                                                    19

<210> SEQ ID NO 19
<211> LENGTH: 19
<212> TYPE: DNA
<213> ORGANISM: Artificial Sequence
<220> FEATURE:
<223> OTHER INFORMATION: Sense oligonucleotide for the CCR3 human
      receptor

<400> SEQUENCE: 19
cagagcactg atggcccag                                                    19

<210> SEQ ID NO 20
<211> LENGTH: 17
<212> TYPE: DNA
<213> ORGANISM: Artificial Sequence
<220> FEATURE:
<223> OTHER INFORMATION: Antisense oligonucleotide inhibiting the CCR3
      human receptor

<400> SEQUENCE: 20
ccctgacata gtggatc                                                      17

<210> SEQ ID NO 21
<211> LENGTH: 17
<212> TYPE: DNA
<213> ORGANISM: Artificial Sequence
<220> FEATURE:
<223> OTHER INFORMATION: Sense oligonucleotide for the CCR3 human
      receptor

<400> SEQUENCE: 21
gatccactat gtcaggg                                                      17

<210> SEQ ID NO 22
<211> LENGTH: 18
<212> TYPE: DNA
<213> ORGANISM: Artificial Sequence
<220> FEATURE:
<223> OTHER INFORMATION: Antisense oligonucleotide inhibiting the CCR3
      rat receptor

<400> SEQUENCE: 22
actcatattc atagggtg                                                     18

<210> SEQ ID NO 23
<211> LENGTH: 18
<212> TYPE: DNA
<213> ORGANISM: Artificial Sequence
<220> FEATURE:
<223> OTHER INFORMATION: Antisense oligonucleotide inhibiting the CCR3
      rat receptor

<400> SEQUENCE: 23
gccaacacag catgaacg                                                     18
```

ANTISENSE OLIGONUCLEOTIDES FOR TREATING ATOPIC DISEASES AND NEOPLASTIC CELL PROLIFERATION

CROSS-REFERENCE TO RELATED APPLICATIONS

This application is a continuation of U.S. Ser. No. 09/719,737 filed on Jun. 29, 2001, now U.S. Pat. No. 6,822,087 issued on Nov. 23, 2004, which was the National Stage of International Application No. PCT/CA99/00572 filed on Jun. 17, 1999 which designated the U.S. and which claims the benefit of Canadian Application No. 2,235,420 filed Jun. 17, 1998.

BACKGROUND OF THE INVENTION (a) Field of the Invention

The invention relates to the use of antisense oligonucleotides directed against specific cellular receptors, alone or in combination, in order to inhibit the inflammatory reaction that is present in asthma, hypereosinophilia or atopic diseases and to inhibit neoplastic cell proliferation.

(b) Description of Prior Art

Antisense oligonucleotides are a new class of pharmaceuticals. In general, antisense refers to the use of small, synthetic oligonucleotides, with the same constituents as that found in our own DNA and which resemble single stranded DNA. The antisense oligonucleotides are designed as a mirror sequence of a part of a gene they are targeting in order to be able to adhere to this sequence and inhibit gene expression. Gene expression is inhibited through hybridization of sense oligonucleotide to a specific messenger RNA (mRNA) sense target according to the Watson-Crick base pairing in which adenosine and thymidine or guanosine and cytidine interact through hydrogen bonding. These simple base-pairing rules govern the interaction between the antisense oligonucleotides and the cellular RNA, which allow to design an antisense oligonucleotide. A major advantage of this new strategy is the specificity of action with the potential for less side effects and toxicity. This therapeutic strategy could potentially be applied to any disease where an overexpression of one or several genes is believed to cause the presence or persistence of the disease. As a result, there have been numerous studies of antisense oligonucleotides as therapeutic agents for cancer and viral diseases.

Few studies have been performed in order to assess whether antisense oligonucleotides could inhibit receptor expression on cell surfaces for inflammatory mediators. Antisense oligonucleotides can be used to inhibit interleukin (IL)-6 receptor expression and thus the effects of the acute inflammatory mediator interleukin-6 on cells. No studies have been conducted to assess whether antisense oligonucleotides can be employed to inhibit receptors on cells that are involved in asthmatic inflammation or on cancerous cells.

Asthma is a disease that affects 5 to 10% of the population which has doubled in prevalence in the last 25 years. This increase has been noted especially in infants after a viral infection of the airways (bronchiolitis), in children and in occupational induced asthma. The exact cause of asthma is not yet known. However, it is believed that agents such as viruses are involved in the perpetuation of the abnormal inflammation that is found in the airways of patients with asthma and thus the persistence of the disease.

For this reason the current recommendations for first line therapy of asthma is a potent anti-inflammatory medication such as corticosteroids and antileukotrienes. Although this therapy is effective in many patients, some patients are resistant to corticosteroids. This medication is also a potent immunosuppressive with long term side effects and has not been shown to be effective in the prevention of allergy or asthma.

Antileukotrienes have some effect in allergy and asthma but are not as effective as corticosteroids.

Several inflammatory mediators play a role in the appearance and perpetuation of inflammation in the airways of patients with asthma. Some mediators attract the inflammatory cells into the airways either through chemotaxis of eosinophils (the chemokines: RANTES, eotaxin 1,2, MCP-3,4 that act mostly in asthmatic inflammation through a receptor called CCR3) or through endothelial cell activation (IL-4,13). Other mediators cause the priming and increased survival of inflammatory cells in the airways (IL-3,5, GM-CSF, IL-4). These mediators thus consist of either specific chemokines for eosinophils or of cytokines of the T helper lymphocyte type 2 phenotype (Th2: IL-3,4,5,13 and GM-CSF).

An improvement in asthma has been shown when there is a decrease in these inflammatory mediators in the airways.

Allergy is a disease that is extremely prevalent, for example atopic rhinitis affects around 30% of the population. Allergy is characterized by abnormal IgE production and inflammation to an allergen. In the presence of IgE and allergen, effector cells such as the mast cells degranulate and release inflammatory mediators leading to the recruitment of the same inflammatory cells that are found in asthma. In atopic rhinitis, nasal polyposis and chronic sinusitis one finds the same excess in inflammatory mediators as those present in asthma. IL-4 and IL-13 are necessary for the production of IgE and the induction of the cells with a Th2 phenotype.

Cancer is the second cause of death in humans and is characterized by abnormal proliferation of immortalized cells. One of the mechanisms that is involved in the persistence and increase in these cells is by the release of growth factors that act through receptors and lead to cellular proliferation. Amongst these growth factors, GM-CSF has been shown to be an important growth factor for several tumor cells. The inhibition of proliferation of cancerous cells by blocking the receptors for growth factors could be important in the therapy of certain cancers.

It would be desirable to be provided with the use of antisense oligonucleotides directed against at least one specific common receptor for either Th2 cytokines or receptor for mediators that attract cells that respond to Th2 cytokines, in order to inhibit the inflammatory reaction that is present in asthma or atopy and to inhibit neoplastic cell proliferation.

It would also be highly desirable to be provided with antisense oligonucleotides directed against a nucleic acid sequence coding for receptors so that by inhibiting these receptors these oligonucleotides could be employed in the therapy and/or prevention of asthma, allergy, general inflammation and cancer.

SUMMARY OF THE INVENTION

One aim of the present invention is to provide the use of antisense oligonucleotides directed against at least one common subunit of a cellular receptor, such as the common beta subunit for IL-3, IL-5, and GM-CSF, or at least one of the common subunits for the IL-4 and IL-13 receptors or the receptor CCR3, in order to inhibit the inflammatory reaction that is present in asthma or atopy and to inhibit neoplastic cell proliferation.

Another aim of the present invention is to provide antisense oligonucleotides directed against a nucleic acid sequence coding for a common subunit of the IL-4 and IL-13 receptors so that by inhibiting these receptors these oligonucleotides could be employed in the treatment and/or prevention of asthma, allergy, general inflammation or cancer.

Another aim of the present invention is to provide antisense oligonucleotides directed against a nucleic acid sequence coding for the common beta subunit of the IL-3, IL-5 and GM-CSF receptors so that by inhibiting these receptors they may be employed in the treatment and prevention of asthma, allergy, hypereosinophilia, general inflammation or cancer.

Another aim of the present invention is to provide antisense oligonucleotides directed against a nucleic acid sequence coding for the CCR3 receptor for chemokines so that by inhibiting this receptor they may be employed in the treatment and prevention of asthma, allergy, general inflammation or cancer.

Another aim of the present invention is to provide a therapeutically effective composition comprising at least two antisense oligonucleotides directed against nucleic acid sequences coding for the common subunits of IL-4 and IL-13 or the common beta subunit of IL-3, IL-5, and GM-CSF, or the CCR3 receptors for a more potent effect in the treatment and/or prevention of asthma, allergy, general inflammation or cancer.

BRIEF DESCRIPTION OF THE DRAWINGS

FIG. 20 illustrates the effect of the antisense directed against the CCR3 receptor (RC86A, called in the figure: CCR3AS 86) on CCR3 mRNA expression in HL60 cells (clone 15) that have been differentiated into the eosinophil pathway;

FIG. 21 illustrates the effect of the antisense RC86A directed against the CCR3 receptor on CCR3 mRNA expression in Ghost cells transfected with the CCR3 receptor;

FIG. 22 illustrates the effect of the phosphorothioate antisense RC86A and the phosphorothioate antisense RC 269 directed against the CCR3 receptor on calcium mobilization in purified human eosinophils;

DETAILED DESCRIPTION OF THE INVENTION

Bronchiolitis is a viral infection of the airways of infants that predisposes to the development of asthma. This condition was studied since it is the earliest one can get in humans prior to the development of asthma, atopy, and allergic inflammation. As is shown hereinafter, an imbalance in the Th1 to Th2 cytokine ratio, favoring Th2 cytokines, is present prior to developing asthma. In one embodiment, the present invention is aimed at restoring this imbalance and thus at preventing or treating asthma and allergies.

Figure 1:
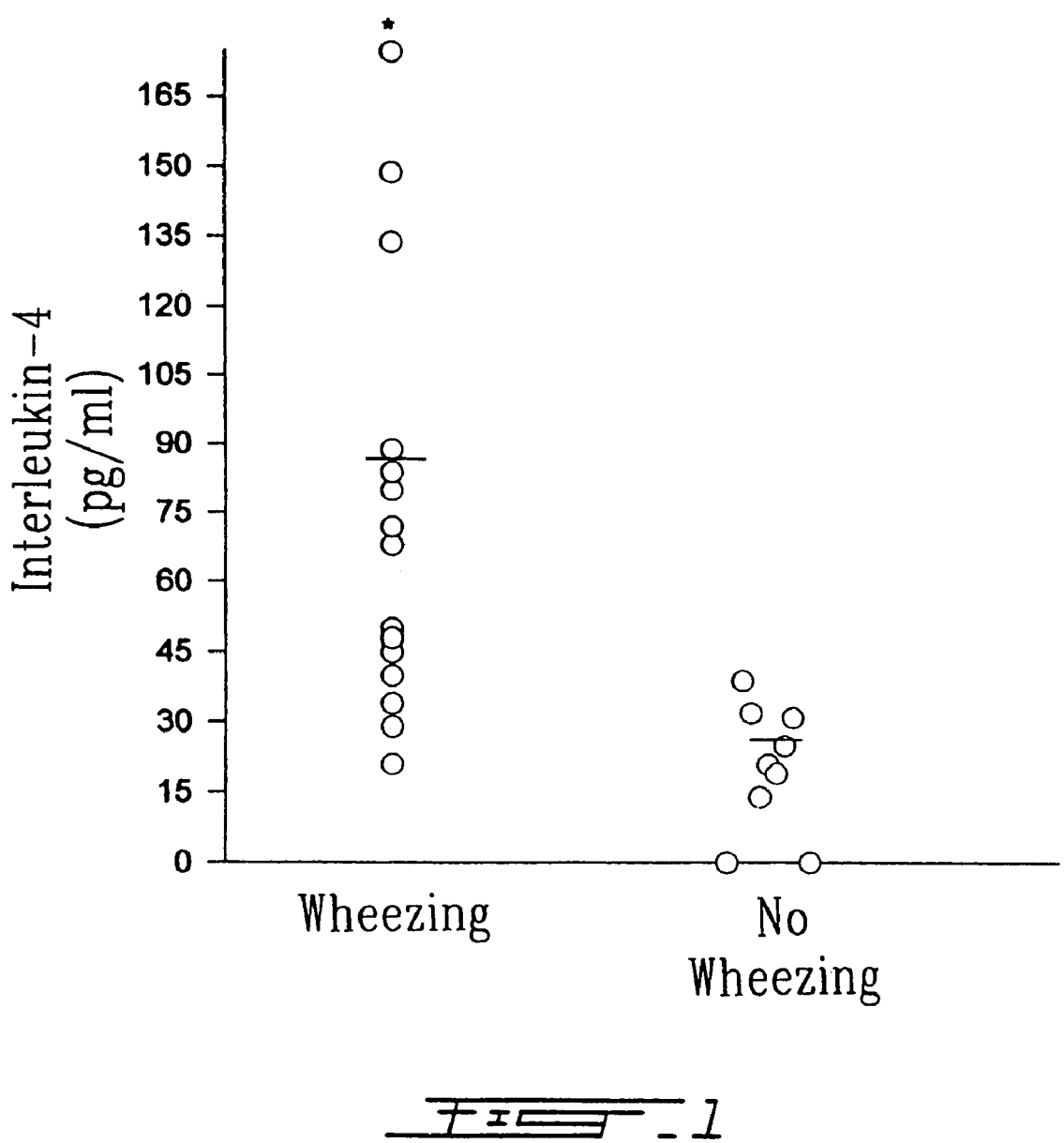
FIG. 1 illustrates increased IL-4 production in response to the house dust-mite antigen in subjects with early wheezing.

Results obtained in lymphocytes isolated from infant blood suffering from bronchiolitis have suggested and confirmed that an imbalance exists between Th1 and Th2 cytokine production prior to the development of early wheezing. Indeed, FIG. 1 shows that lymphocytes from infants who wheeze after bronchiolitis have an increased production of IL-4 (a Th2 cytokine) after exposure to the house dust-mite antigen. In FIG. 1, lymphocytes were isolated from the blood of infants 5 months after bronchiolitis and cultured in the presence of the house dust-mite antigen. IL-4 was measured in the supernatant collected 3 days after culture. Results are presented for the subjects who wheezed for at least one of the last 90 days and those who did not wheeze at all within the first 5 months after bronchiolitis. Asterisk indicates subject who had an IL-4 level of 535 pg/ml. In addition, in infants that wheezed the most in the first five months after bronchiolitis a lower interferon gamma (IFN, a Th1 cytokine) production and a higher IL-4 production was found.

The condition of these infants were monitored for 2 years, pursuant to which it was determined whether they had no asthma, possible asthma or probable asthma by the Delphi consensus. The smoking history and the presence of atopy or asthma in parents or siblings were recorded and blood mononuclear cell IFN and IL-4 production in response to IL-2 were assessed in 32 infants hospitalized for bronchiolitis and in a sub-group (n=19) in which pulmonary function tests were performed 4.9 months later.

Figure 2A:
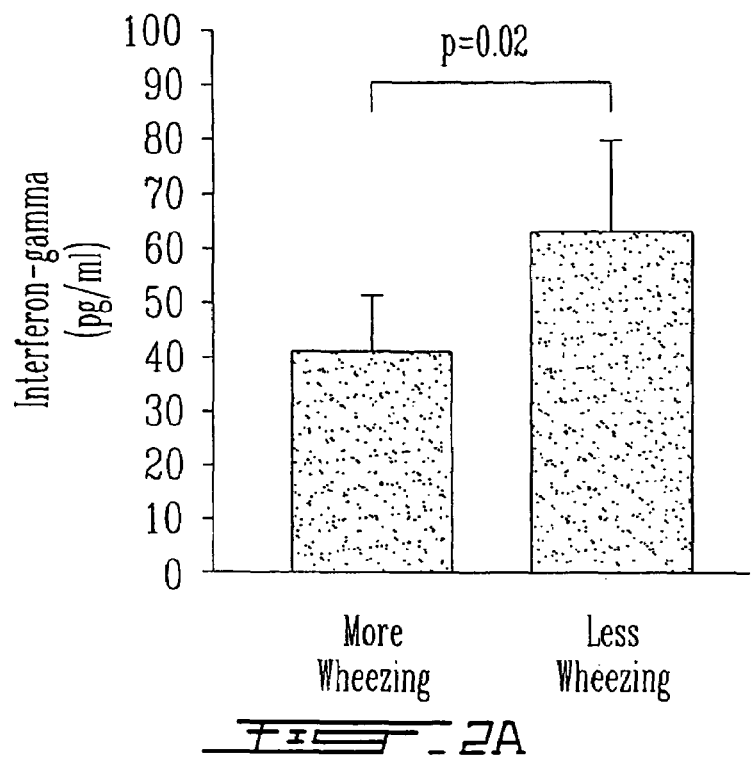
FIGS. 2A and 2B illustrate cytokine production during bronchiolitis as a predictor of the severity of wheezing.
Figure 2B:
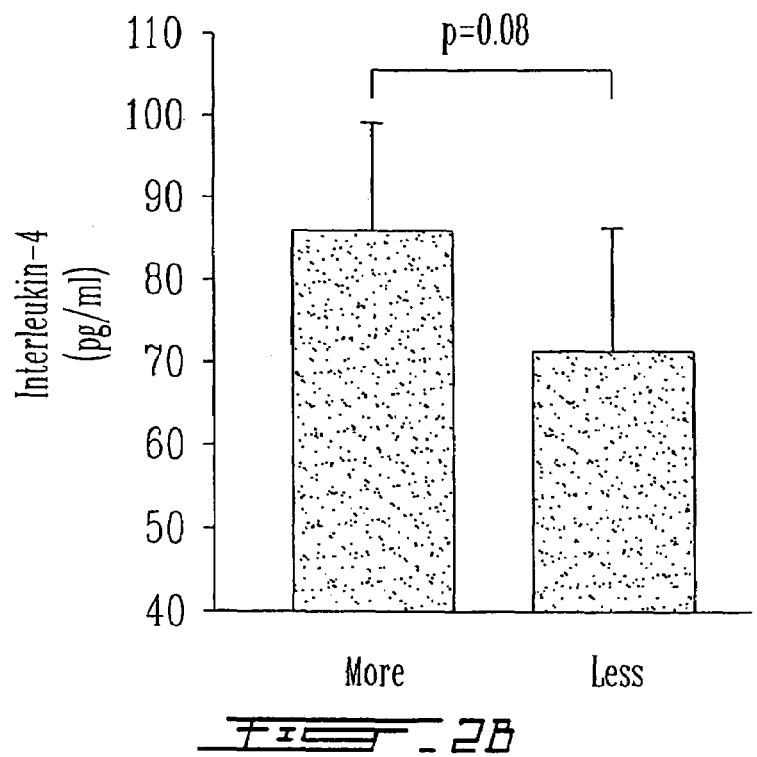

In FIGS. 2A and 2B, lymphocytes were isolated from subjects during bronchiolitis and cultured in the presence of IL-2 for 3 days. The supernatant was collected and the cytokines measured by ELISA. Results are presented for the subjects who wheezed more than 20 days (more wheezing, n=9) and those who wheezed for fewer than 20 days (less wheezing, n=6).

Figure 3A:
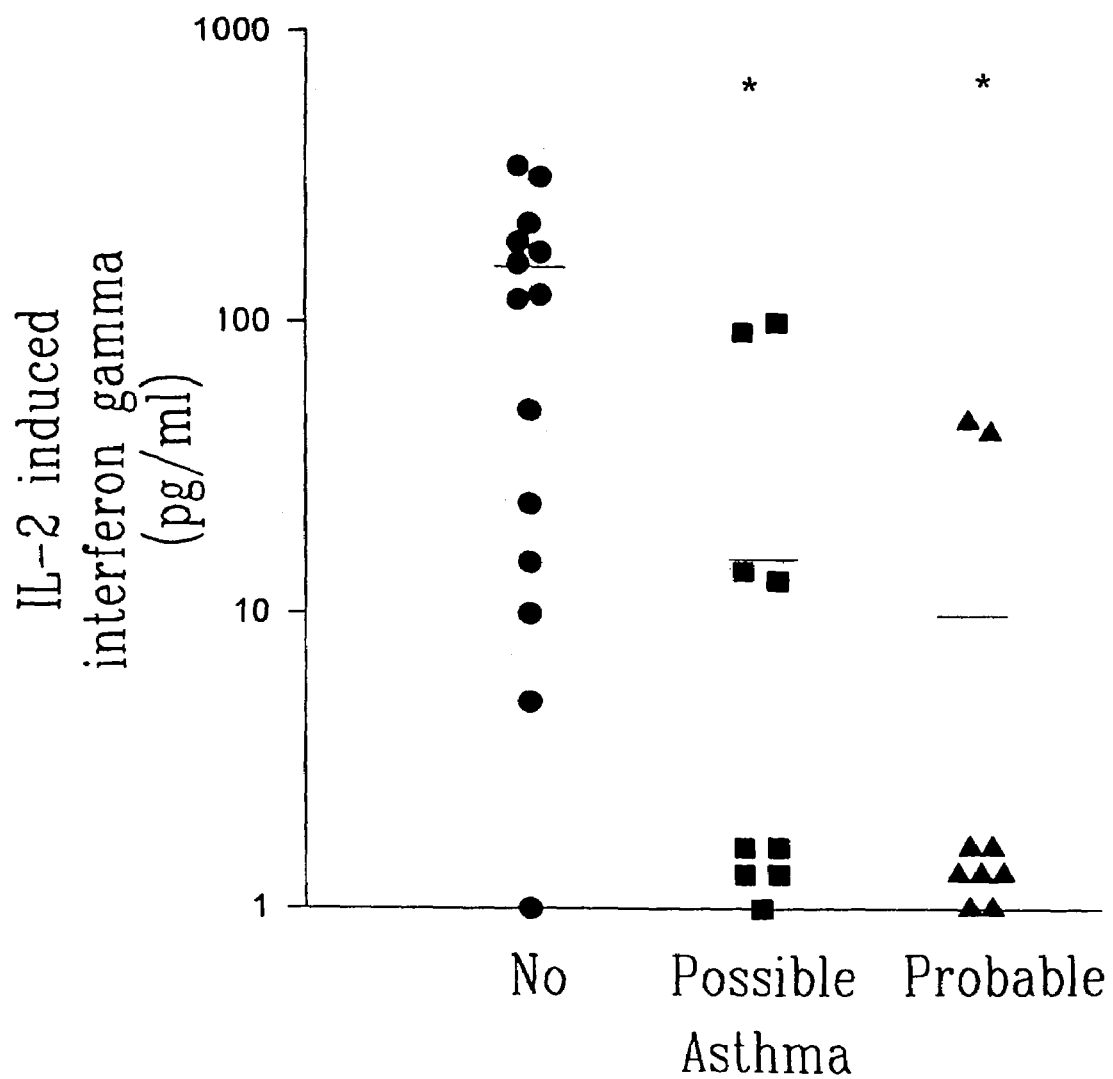
FIGS. 3A and 3B illustrate the relationship between IFN production in response to IL-2 by blood mononuclear cells and the development of asthma 2 years after bronchiolitis in infants.
Figure 3B:
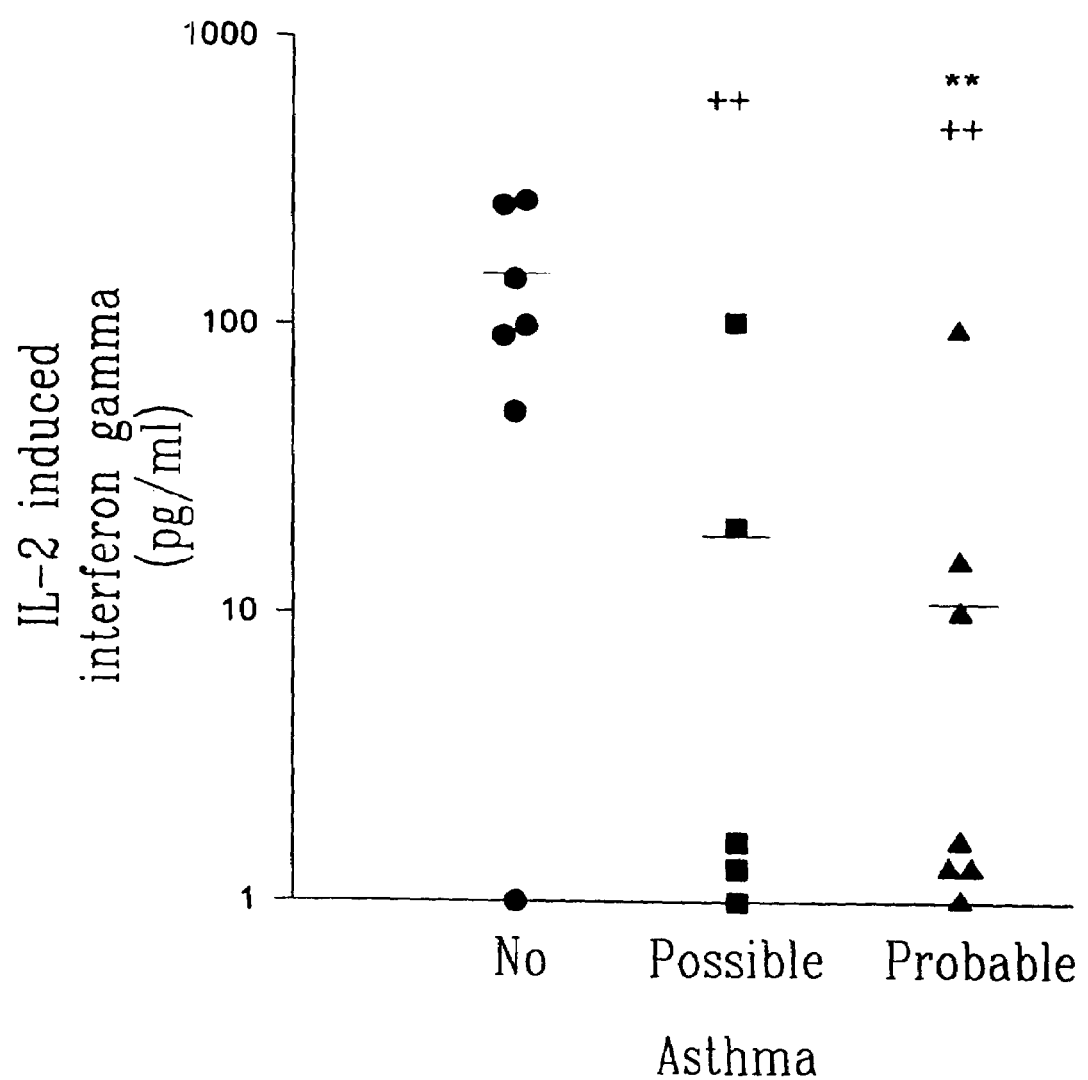

Infants with possible and probable asthma had lower IFN production at the time of, and 4.9 months after bronchiolitis when compared to those who had no asthma (p<0.05, FIGS. 3A and 3B).

In FIGS. 3A and 3B, mononuclear cells obtained at the time of bronchiolitis (3A, n=32) or 4.9 months later (3B, n=19) were partially depleted of monocytes and cultured with IL-2 for 3 days. The supernatant was retrieved and IFN production was measured by ELISA. Results are presented for patients evaluated 2 years after bronchiolitis as having no asthma (no), possible asthma (possible) and probable asthma (probable). For results identified by "*", a probability of p<0.05 was found using the Kruskall-Wallis test and Mann-Whitney U test possible and probable versus no asthma. For results identified by "**", a probability of p=0.08 was found using the Kruskall-Wallis. For results identified by "++", a probability of p<0.05 was found using the Mann-Whitney U test possible and probable asthma versus no asthma.

IL-4 production did not differ between groups. Significant positive correlations were found between IFN production at the time of bronchiolitis and markers of abnormal airway function (Vmax of functional residual capacity (FRC), FIG. 4A)) or of increased airway responsiveness (PC40 histamine, FIG. 4B)), 4.9 months after bronchiolitis.

Figure 4A:
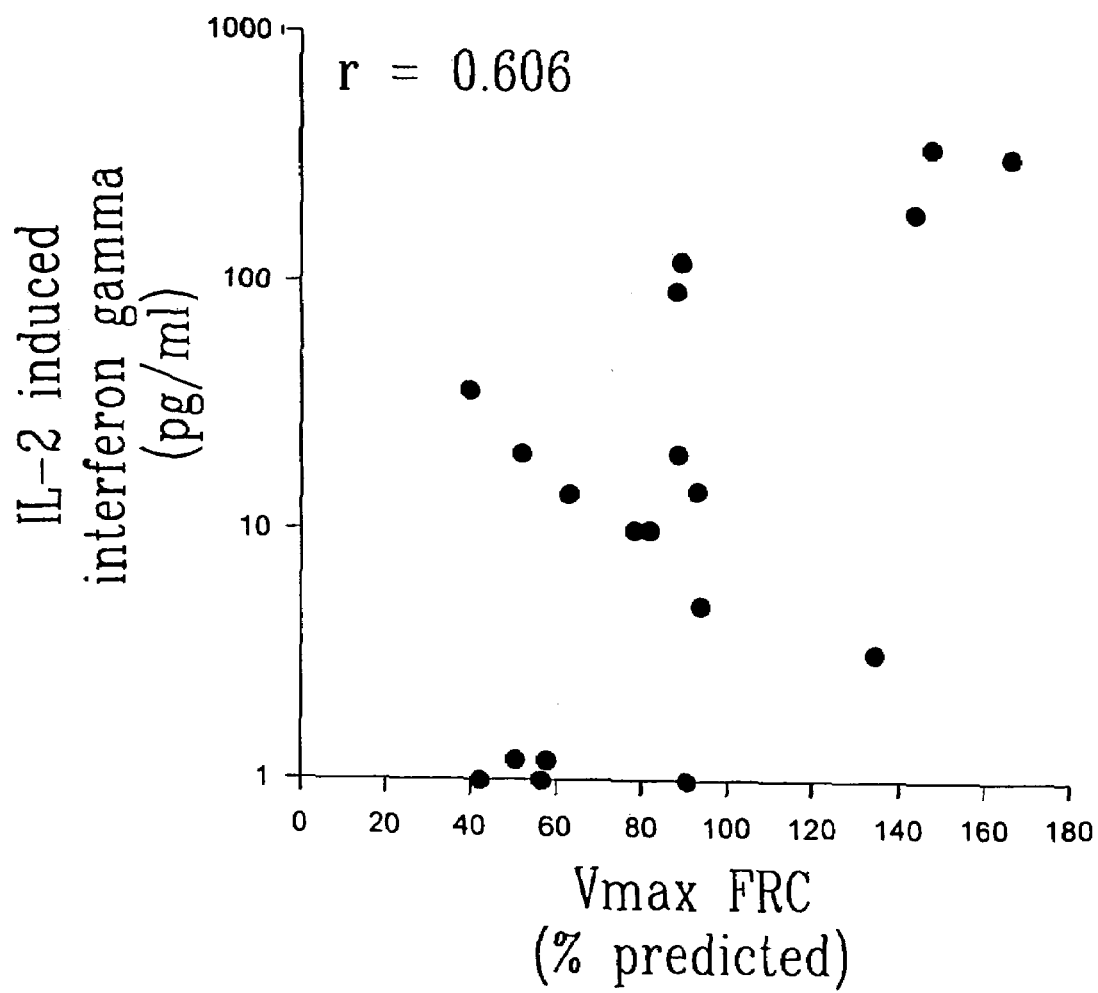
FIGS. 4A and 4B illustrate the correlation between interferon gamma production in response to IL-2 at the time of bronchiolitis in infants and Vmax FRC (4A) or PC40 histamine (4B)
Figure 4B:
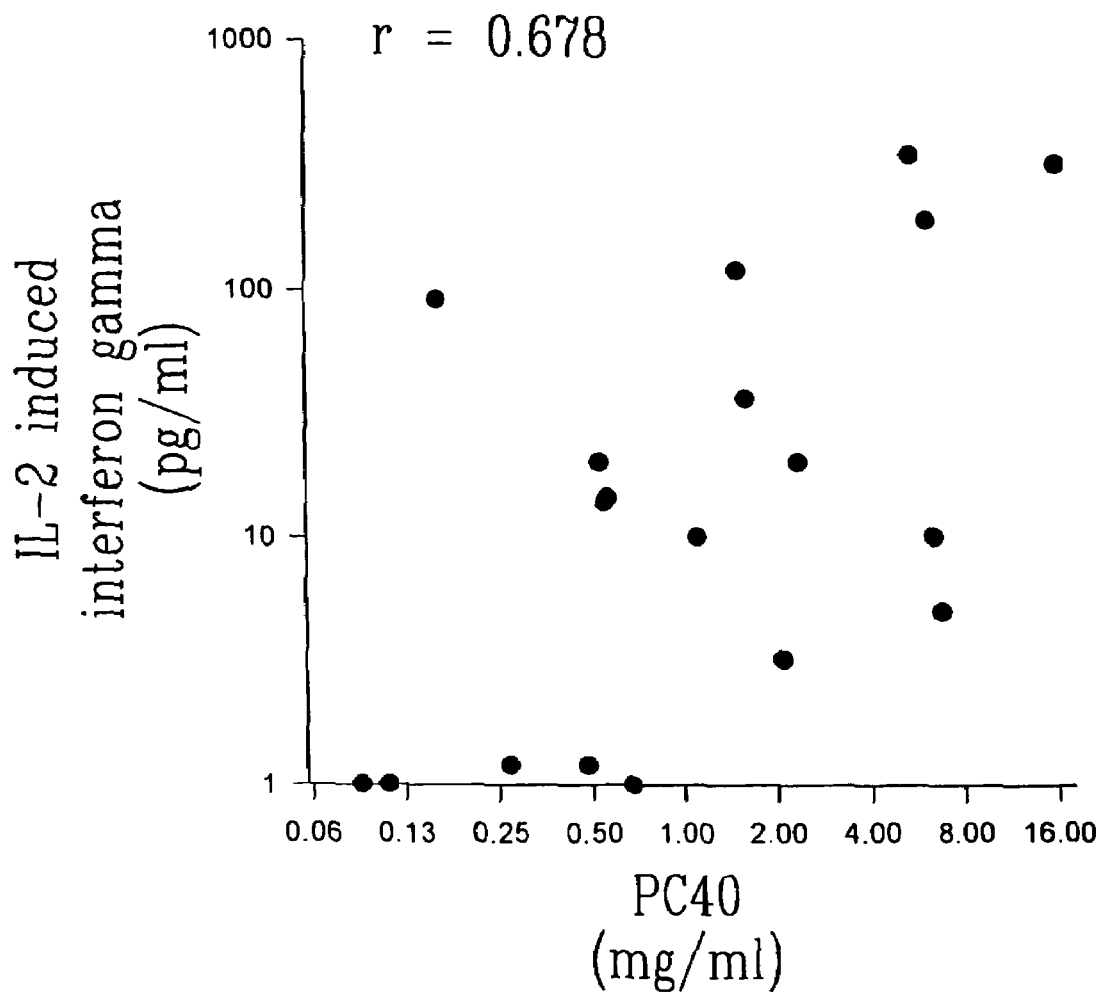

In FIGS. 4A and 4B, cytokine production was measured at the time of bronchiolitis and pulmonary function was measured 4.9 months later. Pulmonary function was evaluated with methods recommended by the American Thoracic Society. Maximal expiratory flow at functional residual capacity (Vmax FRC) was assessed by the rapid thoracoabdominal compression technique (RTC) using the following procedure. Patients previously sedated with chloral hydrate 100 mg/Kg body weight (maximal dose 1000 mg) were placed supine with the neck slightly extended in an inflatable jacket covering the abdomen and thorax and connected to a pressure reservoir. Starting from a pressure of 30 cm H2O and using increments of 5 cm H2O, measurements of expiratory flow at FRC were obtained until Vmax FRC was achieved. Flows were measured with a soft cushion mask connected to a Fleisch no. 1 pneumotachograph and integrated. Three additional technically correct maneuvers were performed at this pressure from which the highest value was chosen to represent baseline Vmax FRC. All subsequent Vmax FRC maneuvers were carried out using the same procedure.

Bronchial reactivity to histamine was assessed by using a Hudson updraft #2 nebuliser driven at 8 liters/min. to administer doubling concentrations of histamine starting at 0.0625 mg/ml to a maximum of 8.0 mg/ml for 1 minute at 5 minute intervals. Vmax FRC was determined after each nebulization. The challenge test ended when a decrease in Vmax FRC of at least 40% from baseline value had been reached, or the maximum concentration of histamine had been given. Heart rate and oxygen saturation were continuously monitored throughout the study with an Ohmeda BIOX 3740 pulse oximeter.

A defect in IFN production is a primary contributor to the development of asthma in infants. Interestingly, this defect is present in adults with asthma and in newborns before they develop atopy. There thus is an imbalance in the relative production of Th2 (IL-4, IL-13, IL-5, etc.) vs. Th1 (IFN) cytokines that is present even before one develops asthma or allergy, the ratio of Th2 over Th1 cytokines is increased prior to the development of and during these diseases.

In order to treat or prevent the development of allergy, asthma or neoplastic cell proliferation that is dependent on an abnormal increase in the production or the effects of Th2 cytokines, it was thus found desirable to decrease the effects of the Th2 cytokines.

Figure 5A:
FIGS. 5A to 5C illustrate the distribution of an FITC labeled antisense phosphorothioate oligonucleotide 8 hours after being nebulized or breathed into the lungs of a rat.

Accordingly, there is provided hereinafter evidence that antisense oligonucleotides according to one embodiment of the present invention, which are breathed into the lungs, are deposited therein, and enter cells where they are active and remain in a non-degraded and thus potent state for at least 24 hours (See FIG. 5 and Example I).

Antisense oligonucleotides according to a preferred embodiment of the present invention are directed against at least one common sub-unit of the IL-4 and IL-13 receptors. These antisense oligonucleotides are effective at inhibiting the functional sub-units of these receptors, as illustrated in Example II.

Antisense oligonucleotides in accordance with another embodiment of the present invention are directed against the common beta sub-unit of the IL-3,5 and GM-CSF receptors. These antisense oligonucleotides are effective at inhibiting these receptors and thus at preventing the proliferation or function of cancerous or inflammatory cells that depend on these growth factors for survival (See Example III).

Antisense oligonucleotides in accordance with another embodiment of the present invention are directed against the CCR3 receptor of chemokines. These antisense oligonucleotides are effective at inhibiting this receptor and thus at preventing the influx, survival and proliferation or function of inflammatory cells and cancerous cells or infectious organisms that depend on this receptor (See Example IV).

The present invention will be more readily understood by referring to the following examples which are given to illustrate the following invention rather than to limit its scope.

EXAMPLE I

Effective Administration of Antisense Oligonucleotides

In order for any therapy to be effective, the administered substance must first find it's way into the lungs and to the cells where it is to have its effects and second, to remain intact without having any side effects. Antisense oligonucleotides breathed into the lungs, are deposited in the lungs and airways to enter the cells where they have their effects and remain in a non-degraded state for at least 24 hours without affecting lung physiology. One microgram (1 µg) of antisense phosphorothioate oligonucleotide of the present invention that had previously been tagged with FITC was administered by nebulization into the lungs of rats. Rats were anesthetized with urethane (1 g/kg, i.p.). A heating pad was used to maintain body temperature constant during the experiment and rectal temperature was monitored continuously with an electronic thermometer. After blind orotracheal intubation with 6 cm of PE-240 polyethylene catheter, pulmonary resistance was measured during spontaneous tidal breathing with the animals in the supine position. Flow was measured by placing the tip of the tracheal tube inside a small Plexiglas® box (265 ml in volume). A Fleisch no. O pneumotachograph coupled to a piezoresistive differential pressure transducer (Micro-Switch 163PCOID36, Honeywell, Scarborough Ont. Canada) was attached to the other end of the box to measure airflow. Transpulmonary pressure (Ptp) was measured using a water-filled catheter placed in the lower third of the esophagus connected to one port of a differential pressure transducer (Transpac II, Abbott, Ill.), the other port being connected to the Plexiglas box. The esophageal catheter consisted of a polyethylene tube (PE-240, 10 cm long) with a terminal tip (6 cm) of a smaller bore tube (PE-160).

The pressure and flow signals were amplified, passed through eight-pole Bessel filters (9 model 902LPF, Frequency Devices, Haverhill, Mass.) with their cut off frequencies set at 100 Hz. The data were stored on a computer. Lung resistance was calculated by multiple linear regression by fitting the equation of motion as performed with commercial software (RHT Infodat Inc. Montreal, PQ).

After instrumentation, an aerosol of saline containing 1 µg of the tagged phosphorothioate oligonucleotide was administered for five minutes. This was generated using a Hudson nebulizer with an output of 0.18 ml/min. connected to one side port of the box. The box was flushed with a stream of fresh air between measurements in order to prevent the accumulation of $CO_2$. Lung resistance was measured 5, 10, 15, 20 and 30 minutes after challenge and subsequently every 15 minutes for a total time of 8 hours. Lung resistance did not change over this time period. The rats were then killed by exsanguination and the lungs retrieved to determine whether the oligonucleotide was still present. The lungs were fixed in paraformaldehyde and an anti-FITC antibody tagged with alkaline phosphatase was used to determine the site of the oligonucleotide, the tissue samples were revealed with fast red and the nucleus of the cells counterstained with a Hoechst counterstain. It is to be noted in FIG. 5A that the oligonucleotides (in red) are present diffusely in all cell types. The oligonucleotides have penetrated the cytoplasm of the cells (5B) and are also found in an inflammatory cell (macrophage, in the middle of 5C).

Figure 6A:
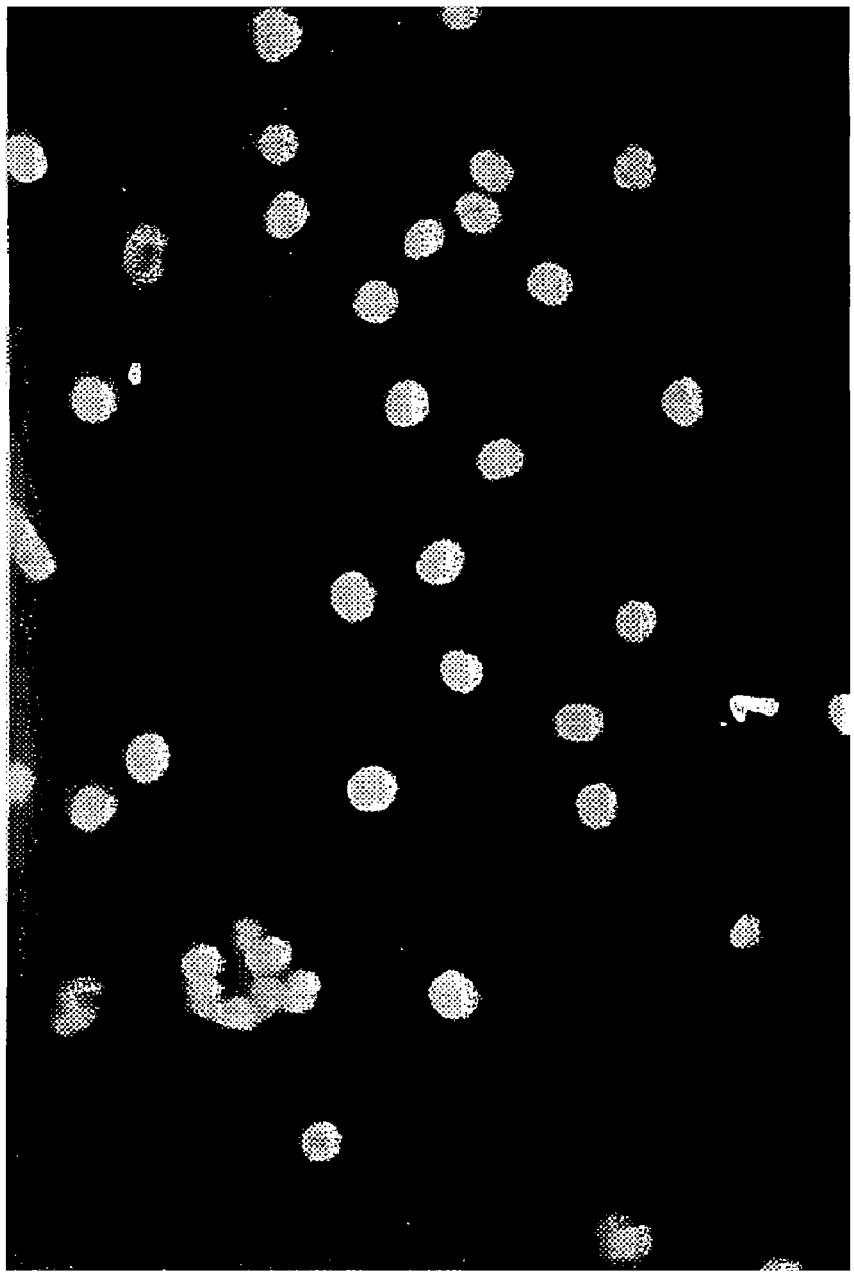
FIGS. 6A and 6B illustrate inflammatory cells (FIG. 6A) and an FITC-labeled antisense phosphorothioate oligonucleotide which has found its way into the inflammatory cells (green fluorescence) (FIG. 6B) retrieved from lung lavage of rats 24 hours after administration.
Figure 6B:
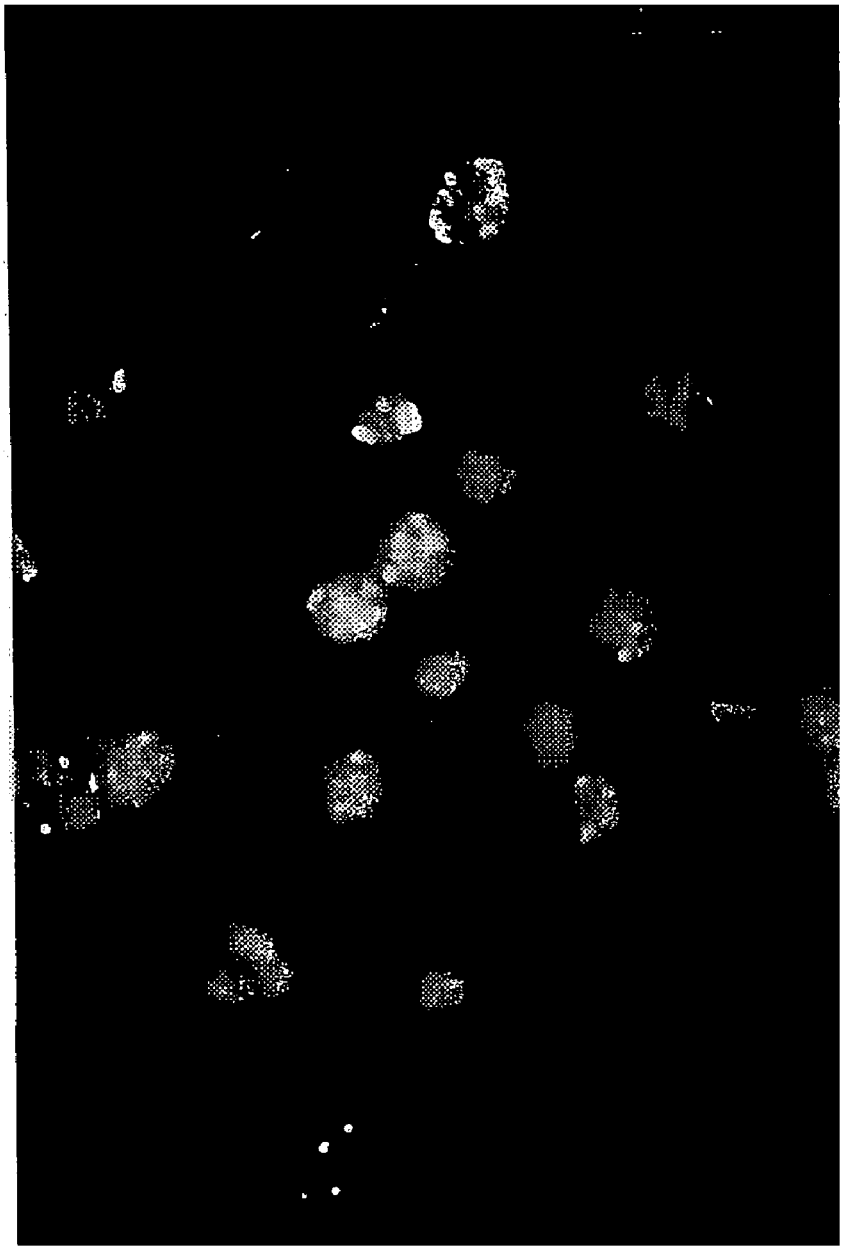

In other experiments, the rats were anesthetized with pentothal and awakened after antisense nebulization. Bronchoalveolar lung lavage (BAL) was performed 24 hours later after general anesthesia by administration of 5 ml of saline and gentle aspiration. The BAL was centrifuged at 400×g for 10 minutes, the supernatant frozen and the cells centrifuged onto slides for analysis. It is to be noted in FIG. 6A that macrophages are the predominant cell type. The FITC-labeled oligonucleotide (green fluorescence) in FIG. 6B is present in the cytoplasm of the cells. The FITC-labeled oligonucleotide was either extracted from the lavage or the lungs of the rats 24 hours after antigen challenge. It is to be noted in FIG. 7 that the antisense oligonucleotide is also intact 24 hours after administration in the BAL (lane 1), lung (lane 2) when compared to it's own control (lane 3) or another oligonucleotide that is tagged with FITC (eotaxin, lane 4).

Figure 5B:
Figure 5C:
Figure 7:
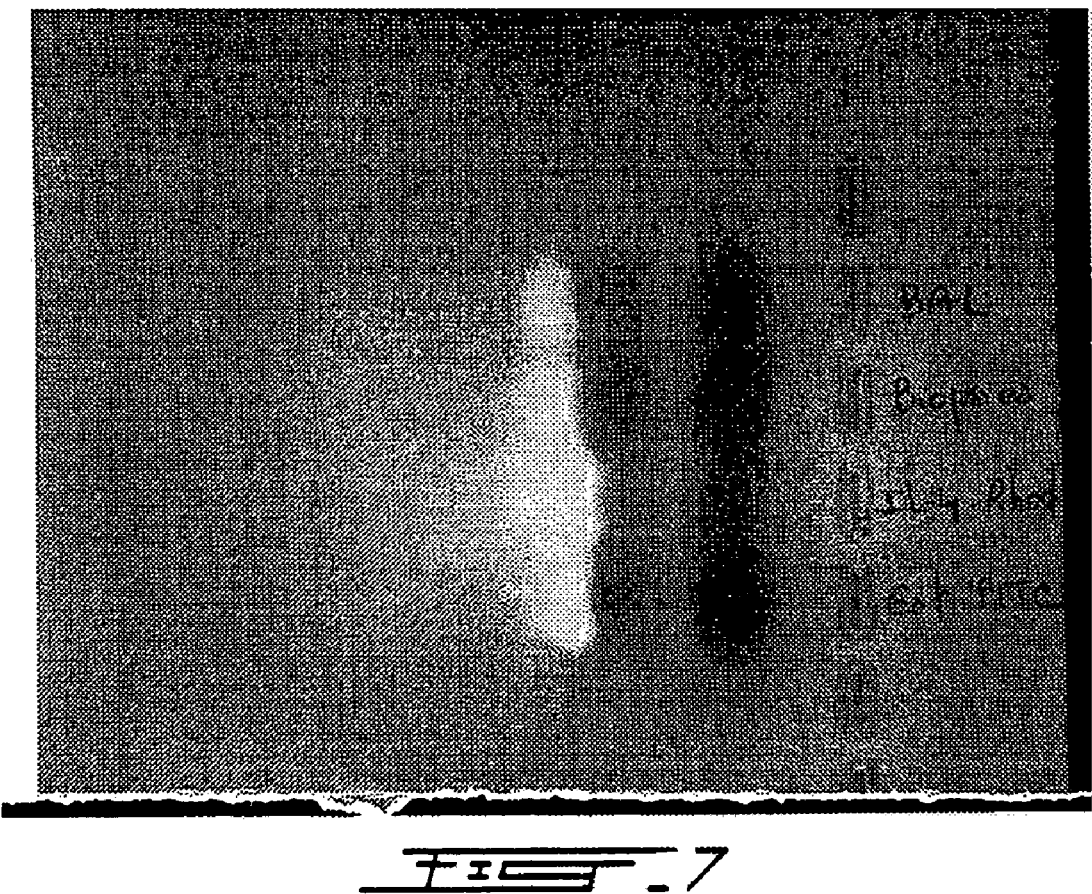
FIG. 7 illustrates a gel showing the antisense phosphorothioate oligonucleotides still intact when retrieved from the bronchoalveolar lavage (BAL) and from the lungs (biopsies) of rats 24 hours after administration when compared to a control antisense oligonucleotide (Eot.FITC)

As can be shown from FIGS. 5 to 7, the antisense oligonucleotides of the present invention are breathed into the lungs, to penetrate the cells, remaining intact for more than 24 hours.

EXAMPLE II

Antisense Oligonucleotides Inhibiting the Common Sub-Units of the IL-4 and IL-13 Receptors Interleukin-4 is involved in IgE production, the development and persistence of asthma and atopy. Although therapies directed against the effects of IL-4 may be effective in the prevention of asthma, allergy or neoplastic cell proliferation (that depends on this mediator), it has recently been shown that another Th2 cytokine (IL-13) has the same effects as IL-4. Interestingly IL-4 and IL-13 share at least two common sub-units which are necessary for signal transduction of the message to occur.

Figure 8:
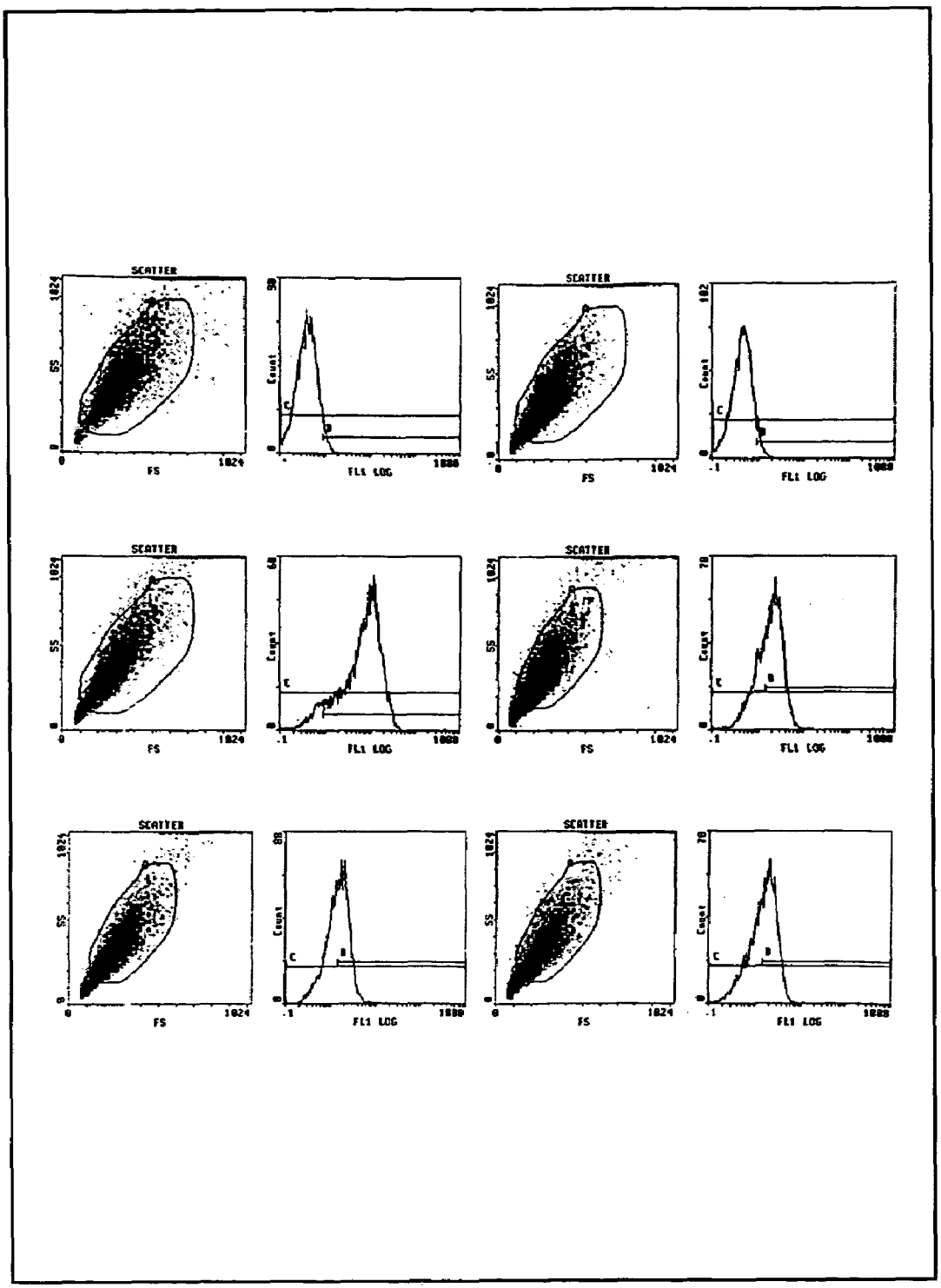
FIG. 8 illustrates the antisense phosphorothioate oligonucleotides OD1, OD2 and OD3 inhibiting IL-4 and IL-13 receptor expression in RAJI cells as detected by Flow cytometry.

Experiments were performed to assess whether antisense oligonucleotides directed against the common sub-units of the IL-4 and IL-13 receptors could inhibit the expression of these receptors. RAJI cells express high levels of IL-4 and IL-13 receptors. These cells were cultured in RPMI 1640 supplemented with 10% heat-inactivated fetal calf serum, penicillin, streptomycin and 1-glutamine at 37° C. in 5% $CO_2$. For 12 hours the cells were either cultured in medium alone or medium with sense or antisense oligonucleotides to the common sub-unit of IL-4/IL-13. The cells were retrieved, washed 3 times and then stained with an anti-human IL-4 receptor antibody (R and D systems, catalog number MAB230), which has been shown to block the human cell surface receptor-mediated bioactivities caused by IL-4 or IL-13. It is to be noted in FIG. 8 that the antisense oligonucleotide OD1: 5'-agaccttcat gttcccagag-3' (SEQ ID NO:1), OD2: 5'-gttcccagag cttgccacct-3' (SEQ ID NO:2) or OD3: 5'-cctg-caagac cttcatgtt-3' (SEQ ID NO:3) inhibits the expression of the bioactive form of the IL-4 receptor when assessed by flow cytometry. The first line shows the absence of fluorescence in cells that were either unstained (left) or exposed to a non-specific monoclonal antibody (right). The second line shows that RAJI cells express the IL-4 receptor (92%) and that the fluorescence intensity is very high (many receptors). On the right, the RAJI cells were incubated for 12 hours with 10 µMol of the antisense oligonucleotide OD1 showing that only 66% of the cells express this receptor and that the fluorescence intensity is very low (few receptors on each cell). The third line shows the same results after 12 hours of incubation with the antisense oligonucleotides OD2 (52%) and OD3 (58%).

Figure 9A:
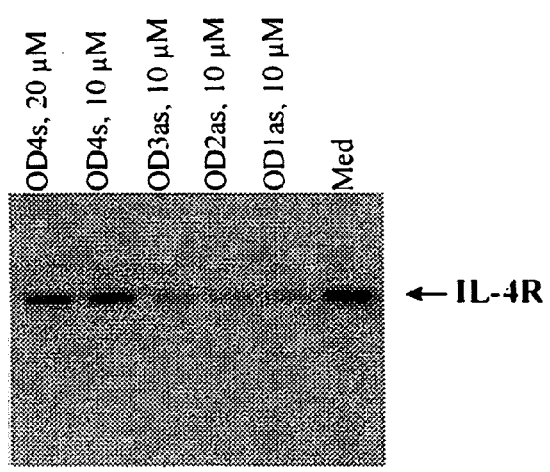
FIGS. 9A and 9B illustrate the antisense phosphorothioate oligonucleotides OD1, OD2 and OD3 in accordance with one embodiment of the invention, inhibiting protein expression of the IL-4 receptor in RAJI cells as detected by immunoprecipitation and Western.
Figure 9B:
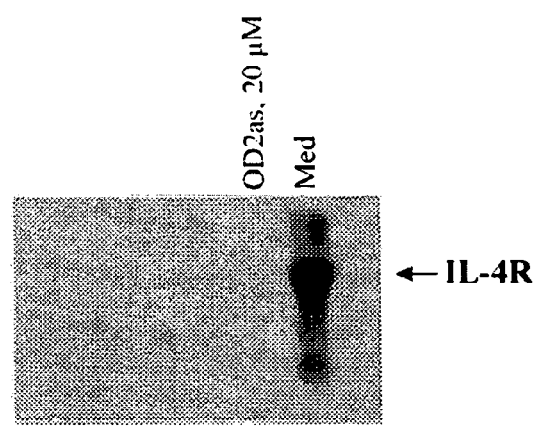

Additional experiments were performed to assess whether antisense oligonucleotides (OD3, OD2 and OD1) inhibited IL-4 receptor expression on RAJI cells by immunoprecipitation and Western blotting. It is to be noted in FIG. 9 that thirty million RAJI cells were cultured for 12 hours as previously described in complete medium with either 20 µM of the sense oligonucleotide OD4 (first lane from the left), 10 µM of OD4 (second lane from the left), 10 µM of the antisense oligonucleotide OD3 (third lane from the left), 10 µM of the antisense oligonucleotide OD2 (fourth lane from the left), 10 µM of the antisense oligonucleotide OD1 (fifth lane from the left), medium alone (sixth lane from the left and last lane on the right of the second gel), 20 µM of the antisense oligonucleotide OD2 (first lane from the left of the gel on the right). The total protein was extracted and incubated with 2 µg of IL-4 overnight. Ten (10) µg/ml of anti-IL-4 antibody (R and D systems) coupled to 50 µl of protein A and Protein G-Sepharose™ was then added for two (2) hours at 20° C. The Sepharose™ beads were washed ten times and an agarose gel was used to separate remaining proteins. The remaining proteins were then transferred onto an Immobilon-P-millipore™ membrane and the Western revealed by a rabbit polyclonal anti-IL-4-R-alpha antibody (Santa Cruz biotechnology, Inc., cat# sc-684). The results show that sense oligonucleotides do not affect IL-4 receptor expression, that 10 µM of the effective antisense oligonucleotides of the present invention inhibit IL-4 receptor expression and that 20 µM of the antisense oligonucleotide OD2 is almost completely effective.

Figure 10:
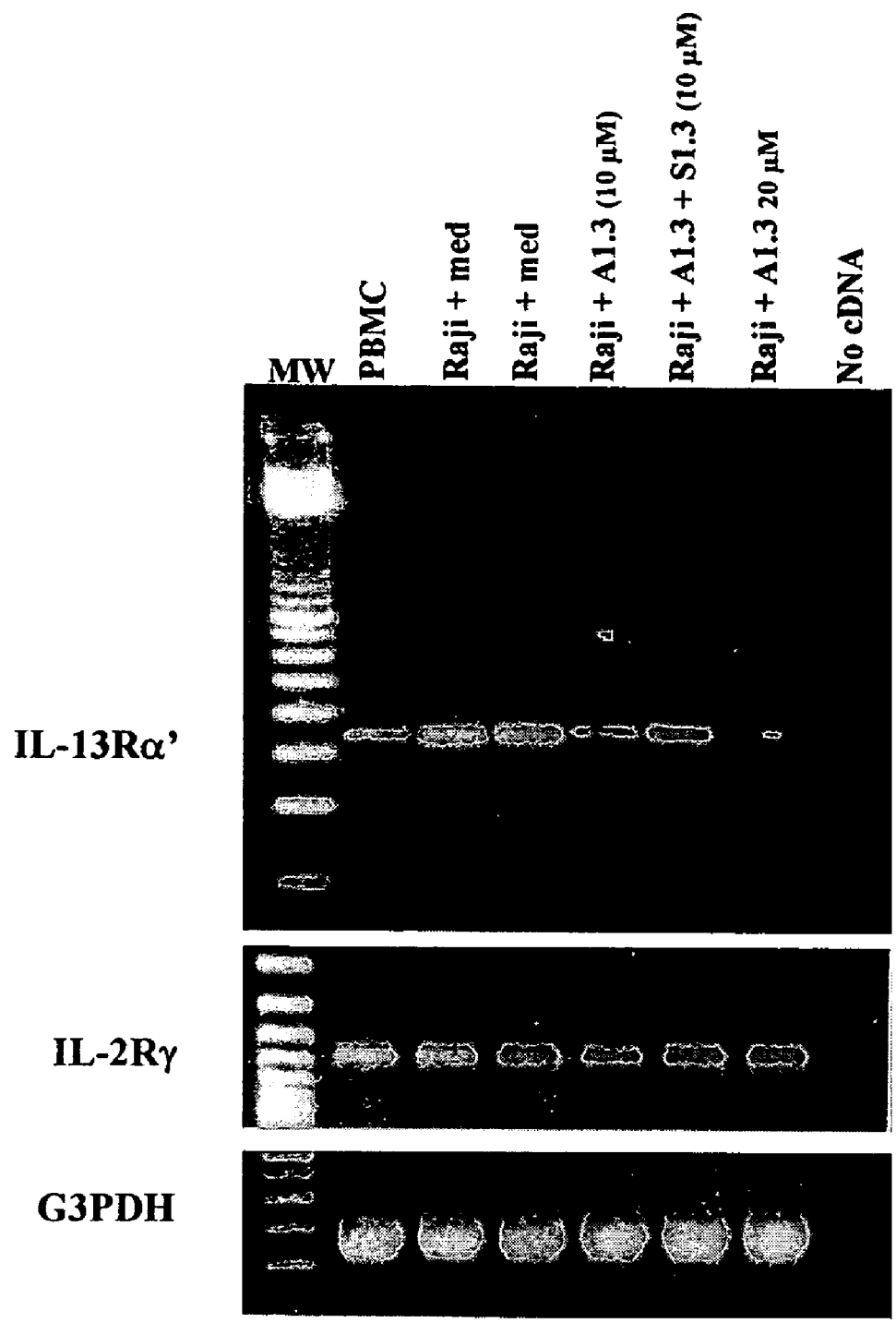
FIG. 10 illustrates the antisense phosphorothioate oligonucleotide A1.3. inhibiting mRNA expression of the alpha' sub-unit of the IL-4/13 receptors.
Figure 11A:
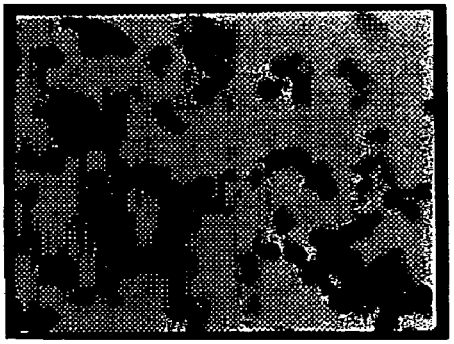
FIGS. 11A to 11F illustrate the dose response of the antisense oligonucleotide OD2 at inhibiting protein expression of the IL-4 and IL-13 receptor in RAJI cells as detected by immunochemistry.
Figure 11D:
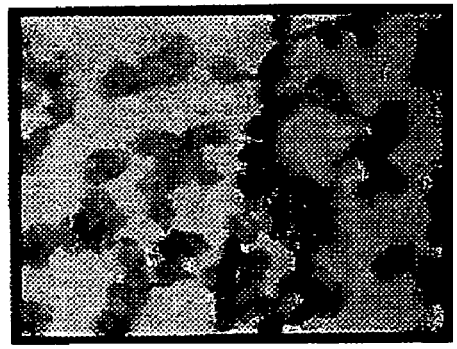
Figure 11B:
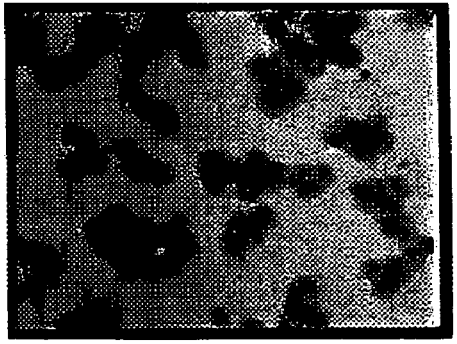
Figure 11E:
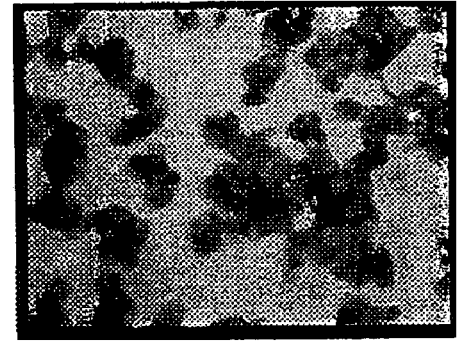
Figure 11C:
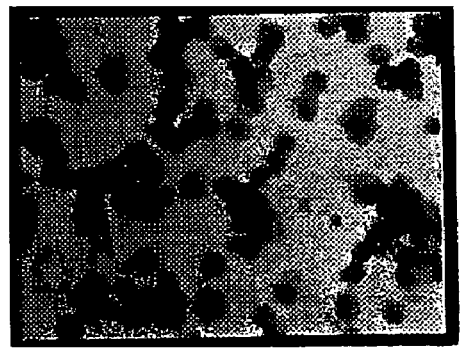
Figure 11F:
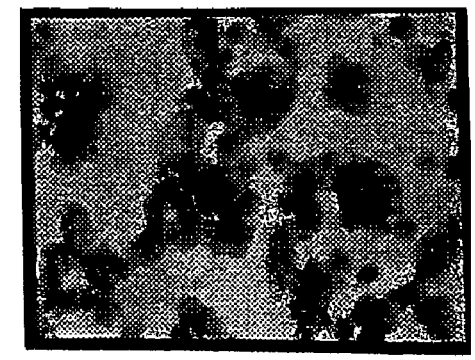

Since there are at least 2 (two) sub-units that are common to the IL-4 and IL-13 -receptors additional experiments were performed to determine whether antisense oligonucleotides directed against the alpha' chain of the IL-13 receptor would also inhibit IL-4/13 receptor expression on RAJI cells. It is to be noted in FIG. 10 that the antisense oligonucleotide A1.3: 5'-CGCCCACAGC CCGCAGAGCC-3' (SEQ ID NO:4) inhibited alpha' receptor expression in RAJI cells. RAJI cells were incubated for 3 hours in medium containing antisense (10 or 20 µM) or sense oligonucleotides (10 µM) and then for 9 hours in complete medium. Thereafter mRNA was extracted. IL-13Ralpha' chain, and controls IL-2Rgamma chain and G3PDH transcripts were assessed by semiquantitative RT-PCR. Results are presented from left to right for peripheral blood mononuclear cells untreated (PBMNC, lane 2), RAJI cells in complete. medium (lanes 3, 4), RAJI cells with 10 µM of A1.3 (lane 5), RAJI cells with 10 µM of A1.3 and its sense counterpart (S1.3, lane 6), RAJI cells with 20 µM of A1.3 (lane 7), and no cDNA (lane 8). Sequences of other antisense oligonucleotides that were also effective in vitro include: A1.1: 5'-CTCCATGCAG CCTCTCGCCT-3' (SEQ ID NO:5); A1.4: 5'-CCGCCGGCGC AGAGCAG-CAG-3' (SEQ ID NO:6); and A1.5: 5'-CGCCCCCGCC CCCGCCCCG-3' (SEQ ID NO:7).

Dose response experiments were performed with the antisense oligonucleotide OD2 to determine the optimal concentration that block IL-4/IL-13 receptor expression in RAJI cells. It is to be noted in FIG. 10 which shows immunostaining experiments that OD2 also inhibited receptor expression when assessed by immunostaining studies. RAJI cells were cultured for 12 hours in complete medium containing 5 µM OD2 (upper left), 10 µM OD2 (middle left), 20 µM OD2 (lower left), no oligonucleotide (upper right), 10 µM of the sense oligonucleotide for the same sequence as OD2 (middle right) or 20 µM of the sense oligonucleotide for the same sequence as OD2 (lower right). Slides were fixed in methanol-acetone at −20° C. for 10 min. After treatment with Tris-buffered saline containing universal blocking solution (DAKO) for 15 min., slides were incubated with an anti-IL-4 receptor serum (Santa Cruz biotechnology, Inc., cat# sc-684) at a final dilution of ½00 overnight at 4° C., followed by incubation with 5 µg/ml alkaline phosphatase-labeled goat anti-rabbit IgG. Nuclei of cells were stained for 1 min. in Haematoxylin. Under these experimental conditions 20 µM of OD2 almost completely inhibited IL-4 receptor expression.

IgE antibody production is an important component of allergy, asthma and certain neoplastic conditions. Experiments were performed to assess the effect of antisense phosphorothioate oligonucleotides directed against the alpha (OD2) and alpha' (A1.3) common sub-units of the IL-4 and IL-13 receptors on IgE production. Human B lymphocytes were isolated from tonsils surgically removed for a variety of indications. Mononuclear cells were purified by Ficoll-Hypaque™ (Pharmacia) density centrifugation. B lymphocytes were separated from T cells by E-rosetting with neuraminidase treated (Calbiochem. La Jolla, Calif.) sheep red blood cells. Monocytes were adherence depleted on plastic petri dishes for 2 hours. B lymphocytes purity was routinely 98%. B cells ($2\times10^5/200$ µl/well) were cultured in complete medium consisting of RPMI 1640, supplemented with 10% FCS, 10 mg/ml L-glutamine, 50 U/ml penicillin, and 50 ng/ml streptomycin. The cells were stimulated with a combination of 200 U/ml of IL-4 (R&D System) and 0.1 µg/ml of anti-CD40 mAb (Pharmingen) in the presence or absence of antisense or sense oligonucleotides at 10 µM for 14 days. Supernatants were harvested and IgE was measured by ELISA (Kallestad, Sanofi Diagnostics, Chaska, Minn.) according to the manufacturer's instructions. It is to be noted in Table 1 that both A1.3 and OD2 antisense phosphorothioate oligonucleotides inhibit human IgE production when compared to their sense counterparts.

TABLE 1

Inhibition of IgE production by antisense oligonucleotides in anti-CD40 + IL-4 stimulated human B cells

|  | IgE in pg/ml |
| --- | --- |
| Medium | <200 |
| Anti-CD40 + IL-4 | 1109 |
| + A1.3 (antisense 10 µM) | 122 |
| + A1.3 (strand sense 10 µM) | 1001 |
| + OD2 (antisense 10 µM) | 364 |
| + OD2 (strand sense 10 µM) | 1039 |

Figure 12:
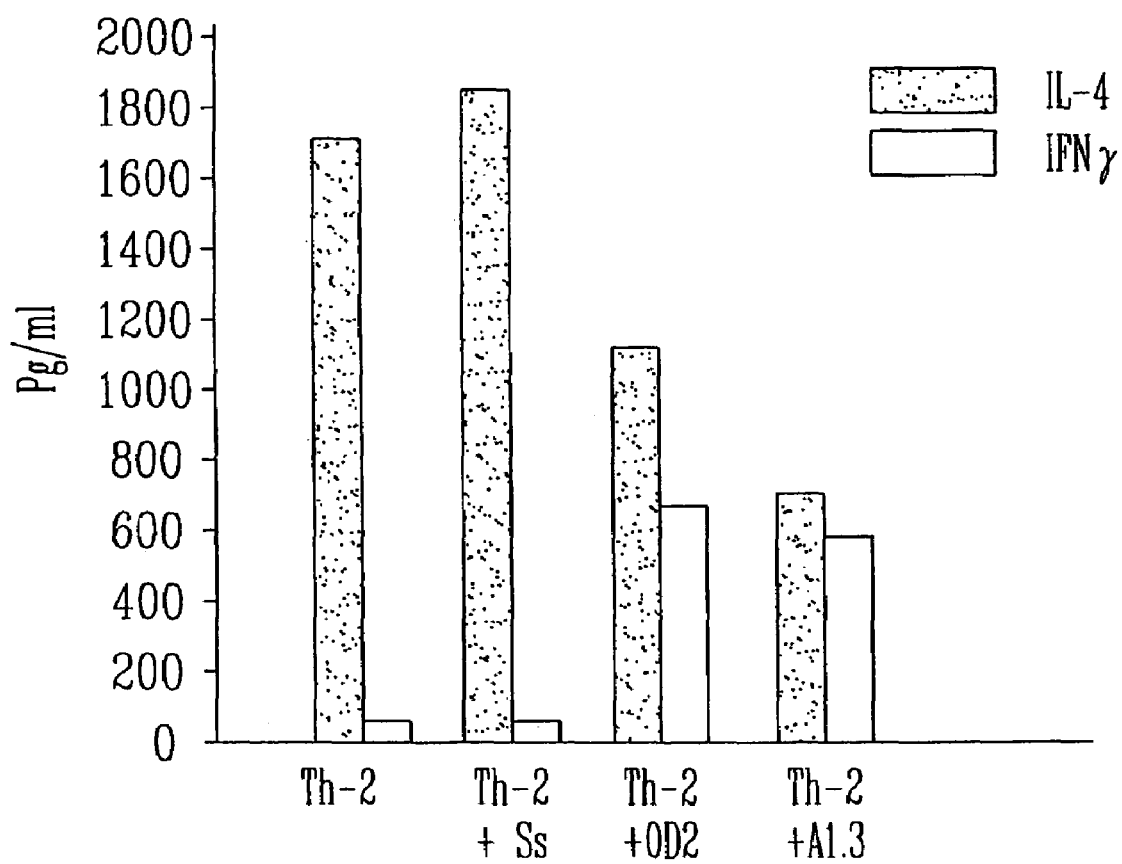
FIG. 12 illustrates the antisense phosphorothioate oligonucleotides OD2 and A1.3 inhibiting IL-4 and increasing IFN-γ production in human umbilical cord blood cell Th-2 progenitor cells.

As mentioned previously, an imbalance between production of the Th-2 cytokine interleukin-4 and the Th-1 cytokine IFN-γ has been described in allergy and asthma. Experiments were performed to assess the effect of antisense phosphorothioate oligonucleotides directed against the alpha (OD2) and alpha' (A1.3) common sub-units of the IL-4 and IL-13 receptors on IL-4 and IFN-γ production. Human mononuclear cell suspensions were obtained from umbilical cord blood (UCB) by centrifugation over Ficoll-Hypaque™ gradient at 400 g for 30 minutes. Monocytes were depleted by adherence to plastic flasks during 2 hours at 37° C. in RPMI 1640 supplemented with 7.5% fetal calf serum (FCS) in a 5% $CO_2$ incubator. Cord blood T cells were stimulated with PHA (1 µg/ml) under TH1 polarizing conditions [human rIL-12 (2 ng/ml; R&D Systems) plus neutralizing mAb to IL-4 (200 ng/ml.; R&D Systems)] or TH2 polarizing conditions [human recombinant IL-4 (200 U/ml) plus neutralizing mAb to human IL-12 (2 µg/ml; R&D Systems)] in the presence or absence of 10 µM of antisense or sense oligonucleotides. Each oligonucleotide was added to the culture 3 hours before the addition of the cytokines. IL-2 was added at day 3. After 1 and 2 weeks, the cultures were restimulated in the same polarizing conditions in the presence or absence of oligonucleotides and analyzed after 10 days of culture. Cells were harvested, washed three times and restimulated with PMA (50 ng/ml) plus ionomycin (500 ng/ml) for 48 h at 37° C., for analysis of IL-4 and IFN-γ production in supernatants by ELISA (R&D Systems) according to the manufacturer's instructions. It is to be noted in FIG. 12 that antisense oligonucleotides directed against the common sub-units of the IL-4/13 receptors inhibit IL-4 production and increase IFN-γ production. From left to right, purified UBC were cultured in Th-2 stimulating conditions: Th-2 stimulating conditions in the presence of the sense oligonucleotide for OD2; Th-2 stimulating conditions in the presence of the antisense oligonucleotide OD2 and Th-2 stimulating conditions in the presence of the antisense oligonucleotide A1.3.

As can be shown from FIGS. 8 to 12, the antisense oligonucleotides of the present invention directed against the common sub-units alpha and alpha' of the IL-4/IL-13 receptor are effective at inhibiting IL-4/13 receptor expression, their functional component, IgE production and the switching of progenitors to Th-2 type cells.

EXAMPLE III

Antisense Oligonucleotides Inhibiting the Common Beta Sub-Unit of IL-3, IL-5 and GM-CSF Receptors Interleukin-3, 5 and GM-CSF are important cytokines that are involved in eosinophil proliferation and survival. These cytokines are increased in asthma and atopic diseases and are also involved in the indefinite proliferation of certain neoplastic diseases. Interestingly, IL-3, IL-5 and GM-CSF share a common beta sub-unit that is involved in signal transduction.

Figure 13A:
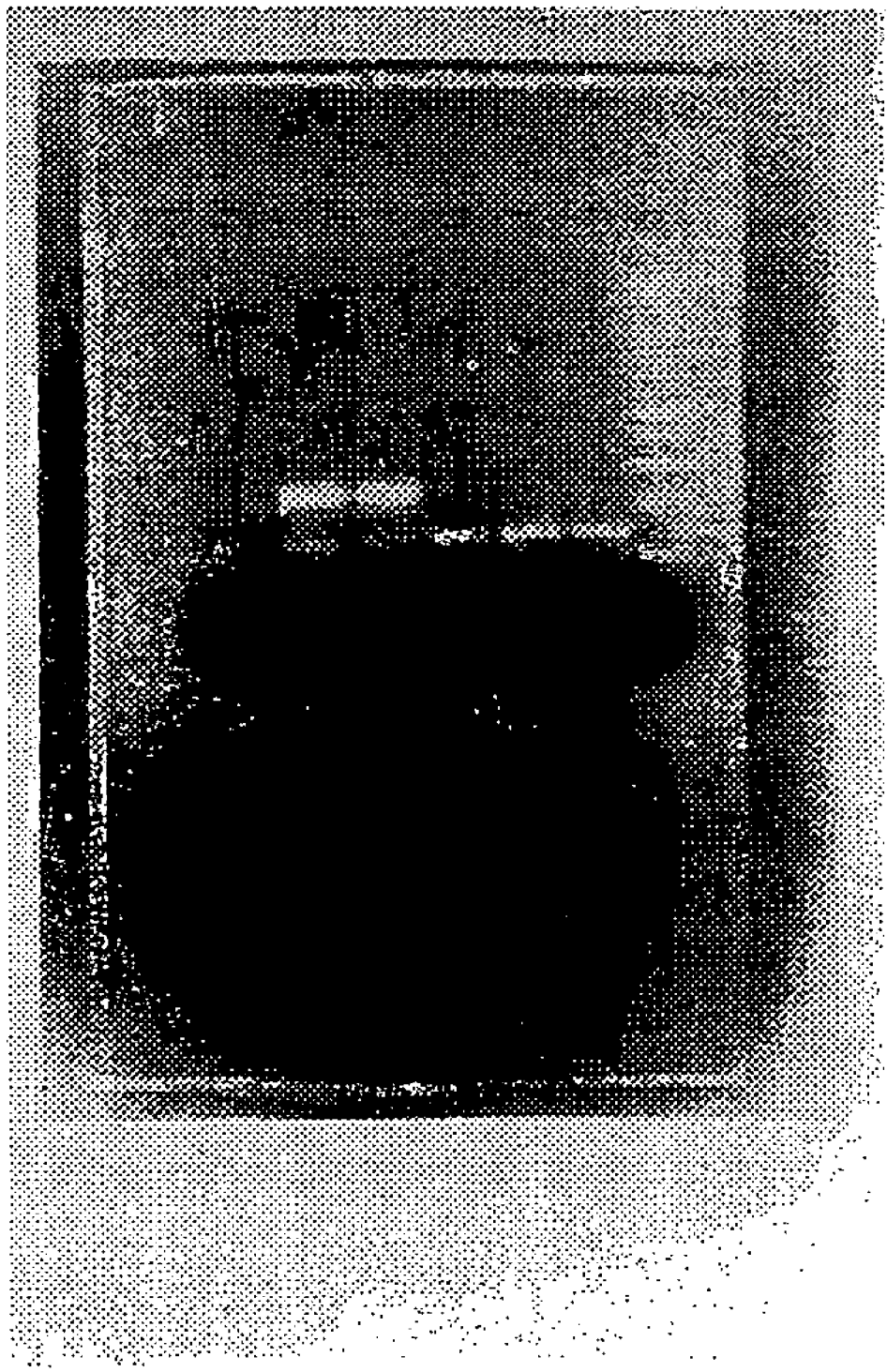
FIGS. 13A and 13B illustrate the antisense phosphorothioate oligonucleotide 107A inhibiting mRNA expression (by semi-quantitative RT-PCR) of the common beta sub-unit of the IL-3, IL-5 and GM-CSF receptor in TF1 (FIG. 13A) and U937 (FIG. 13B) cells.
Figure 13B:
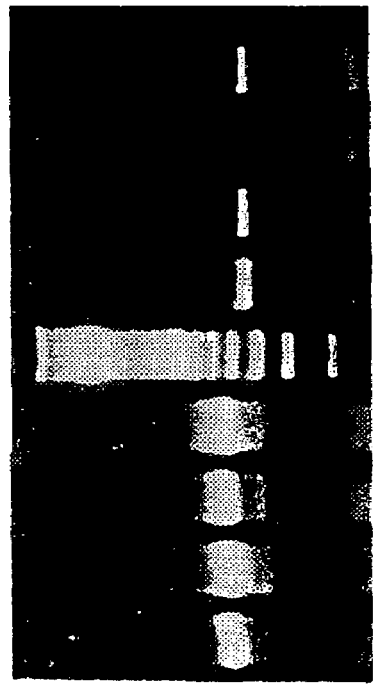

Experiments were performed to assess whether antisense oligonucleotides of the present invention, directed against the common beta sub-unit of the IL-3, IL-5 and GM-CSF receptor, could inhibit the expression and the function of this receptor. TF-1 and U937 cells express high levels of GM-CSF receptors. In addition, TF-1 cells are dependent on GM-CSF for survival. These cells were cultured in RPMI 1640 supplemented with 10% heat-inactivated fetal calf serum, penicillin, streptomycin and 1-glutamine at 37° C. in 5% $CO_2$ (the TF-1 cells were supplemented with GM-CSF). For 12 hours they were either cultured in medium alone or medium with sense (107S: 5'-ACCATCCCGC TGCAGACCC-3' (SEQ ID NO:8)) or antisense (107A: 5'-GGGTCTGCAG CGGGATGGT-3' (SEQ ID NO:9)) oligonucleotides to the common beta sub-unit of the IL-3, IL-5 and GM-CSF receptor. The cells were retrieved and washed 3 times. RNA was then retrieved and the presence of the beta chain of the receptor was assessed by semi-quantitative RT-PCR. It is to be noted in FIG. 13 that the antisense oligonucleotides inhibit the expression of mRNA for the common beta receptor in TF1 cells (13A) and U937 cells (13B). In FIG. 13A, read from left to right, mRNA expression for Beta actin is shown in control, sense, and antisense treated cells (lanes 2,3,4); mRNA expression for the common receptor is shown in control, sense and antisense treated cells (lanes 5,6,7). The absence of a band in lane 7 is indicative of the effectiveness of the antisense oligonucleotide at inhibiting mRNA expression of the common Beta sub-unit in TF1 cells. In FIG. 13B, read from the right to left, mRNA expression for the common beta sub-unit is shown in mismatch, antisense, sense and control (non treated) cells (lanes 1,2,3,4); mRNA expression for G3PDH is shown in mismatch, antisense, sense and control (non treated) cells (lanes 6,7,8,9). The absence of a band in lane 2 is indicative of the effectiveness of the antisense oligonucleotide at inhibiting mRNA expression of the common Beta sub-unit in U937 cells.

Figure 14:
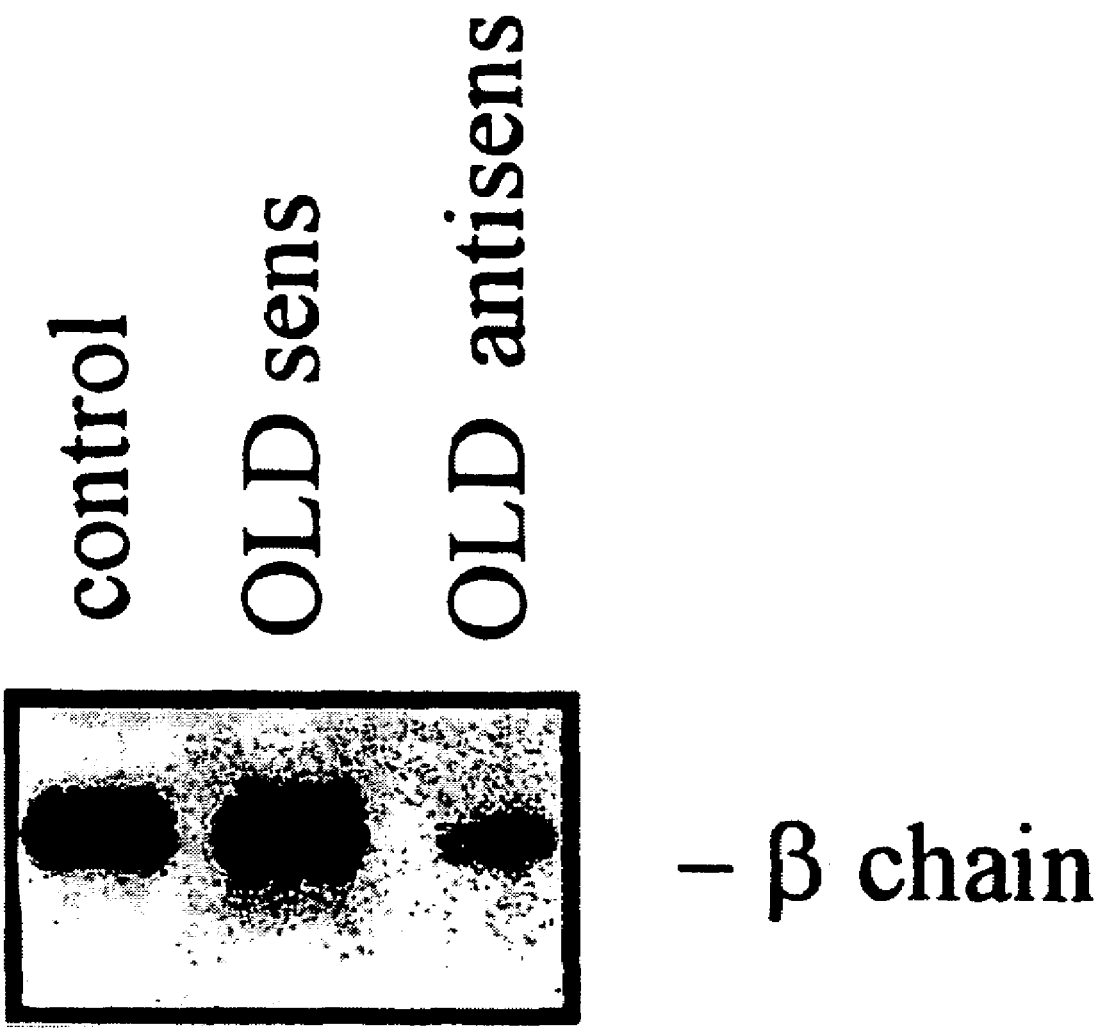
FIG. 14 illustrates the antisense phosphorothioate oligonucleotide 107A inhibiting protein expression of the common beta sub-unit of the IL-3, IL-5 and GM-CSF receptors in TF1 cells as detected by immunoprecipitation and Western.

Additional experiments were performed to assess whether antisense oligonucleotides (107A) inhibited the common beta sub-unit of IL-3, IL-5 and GM-CSF receptors in TF1 cells by immunoprecipitation and Western blotting. In FIG. 14, thirty million TF1 cells were cultured for 12 hours as previously described in complete medium with either 10 μM of the sense oligonucleotide 107S or the antisense oligonucleotide 107A (first lane from the right). The protein was extracted by immunoprecipitation with a monoclonal antibody against the GM-CSF beta chain receptor. The extracts were then transferred onto an Immobilon-P-millipore membrane after electrophoresis on a polyacrylamide gel, and the GM-CSF beta chain of the receptor was then revealed by a rabbit polyclonal anti-GM-CSF-R-Beta antibody. The results show that, at the same concentration (10 μM), sense oligonucleotides do not affect the common beta chain expression, while the antisense oligonucleotides of the present invention inhibit the common beta sub-unit of IL-3, IL-5 and GM-CSF receptors.

Figure 15:
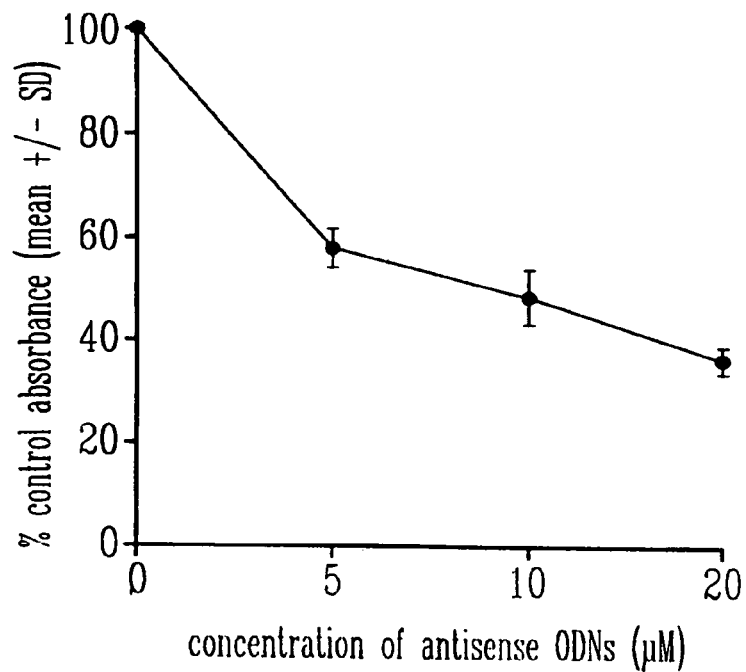
FIG. 15 illustrates the antisense phosphorothioate oligonucleotide 107A inhibiting as a dose response TF1 cell proliferation.

Dose response experiments were performed with the antisense oligonucleotide 107A to determine the optimal concentration that would block TF1 cell growth. As seen in FIG. 15, antisense oligonucleotides of the present invention can be used to inhibit cell growth. TF1 cells were cultured in the presence of increasing concentrations of the oligonucleotides in serum free medium for 2 hours and then fetal bovine serum and GM-CSF were added to a final concentration of 10% and 1 ng/ml, respectively. The culture was performed for an additional 2 days and then cells were assayed for their capacity to reduce MTT dye over a four (4) hour period to a colored formazan product as an index of cell survival and proliferation. The results are expressed as a percentage of absorbance of MTT-derived formazan developed by untreated cells. Dot=mean±SDEV. The experiment was performed in triplicate. Absorbance was read at 570-595 nm.

Figure 16:
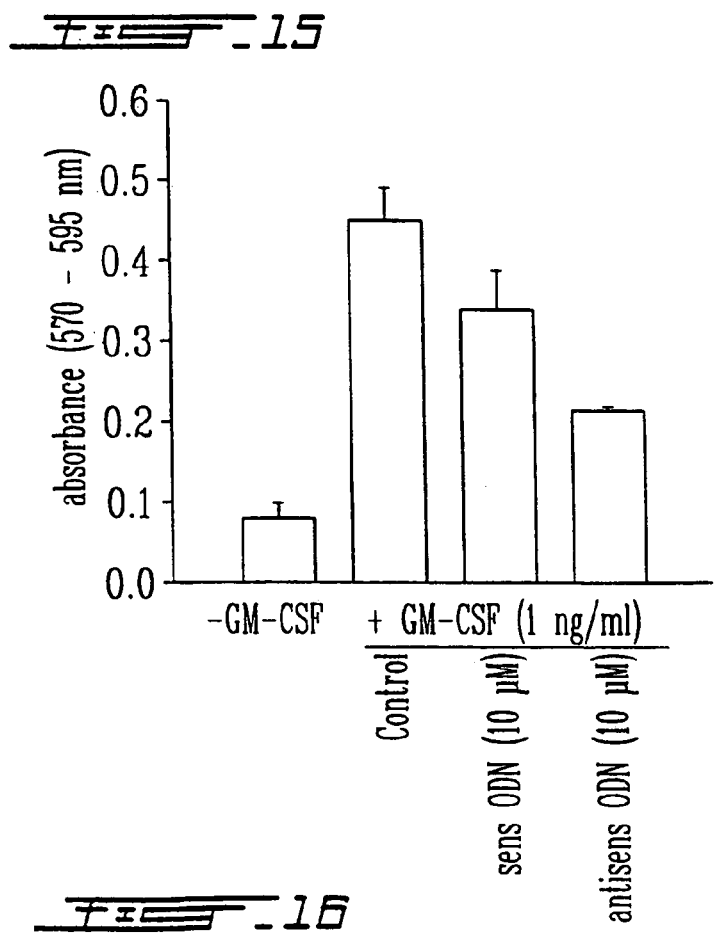
FIG. 16 illustrates the antisense phosphorothioate oligonucleotide 107A inhibiting TF1 cell growth.

It is to be noted in FIG. 16 that the antisense oligonucleotide 107A can significantly inhibit cell growth when compared to the sense probe or a control without antisense oligonucleotides. TF1 cells were cultured in the presence of the antisense oligonucleotide (first from right), the sense oligonucleotide (2nd from right), control medium (including GM-CSF, 3rd right) or medium without GM-CSF 4th from right) for 2 days and then cells were assayed for their capacity to reduce MTT dye as described above.

Other antisense oligonucleotides in accordance with the present invention have shown effectiveness at a concentration of 20 μMol. These antisense oligonucleotides are for example, but without limitation, the oligonucleotides 106: 5'-ggtctgcagc gggatggtt-3' (SEQ ID NO:10); 108: 5'-agggtctgca gcgggatgg-3' (SEQ ID NO:11); 110: 5'-gcagggtctg cagcgggat-3' (SEQ ID NO:12); 101: 5'-gcagcgggat ggtttcttc-3' (SEQ ID NO:13); 100: 5'-cagcgggatg gtttcttct-3' (SEQ ID NO:14); and 105: 5'-gtctgcagcg ggatggttt-3' (SEQ ID NO:15).

Figure 17:
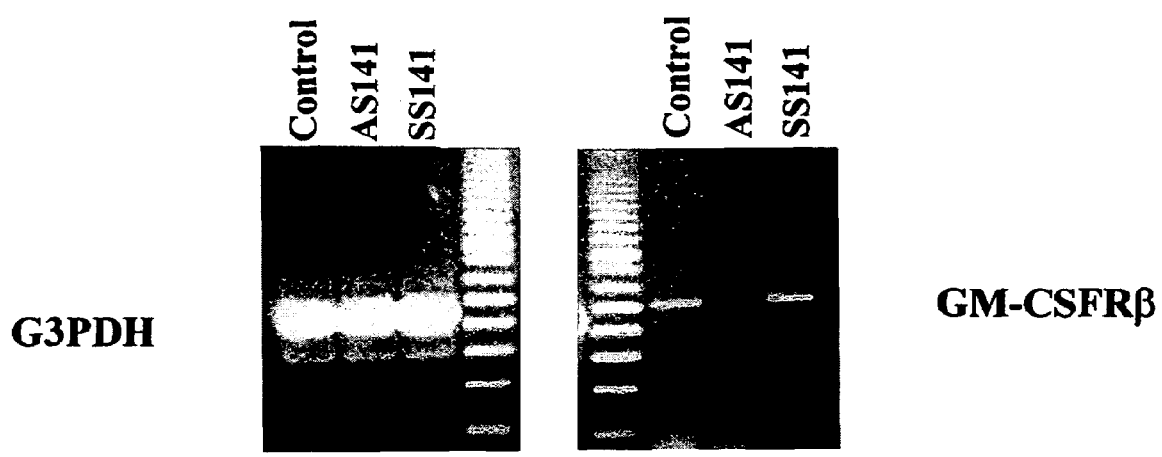
FIG. 17 illustrates the antisense phosphorothioate oligonucleotide RB141A (also referred to as AS141) inhibiting mRNA expression of the beta sub-unit of the GM-CSF, IL-3 and IL-5 receptors in rat bone marrow cells.

Experiments were performed to determine whether antisense oligonucleotides directed against the common beta chain of the GM-CSF, IL-3 and IL-5 receptors could inhibit the influx of eosinophils in vivo. It is to be noted in FIG. 17 that the antisense oligonucleotide RB141A: 5'-TGGCACTTTA GGTGGCTG-3' (SEQ ID NO:16) is effective at inhibiting mRNA expression of rat common beta chain of the GM-CSF, IL-3 and IL-5 receptors in vitro. On the left are results of semi-quantitative RT-PCR for the G3PDH gene in control, RB141A and sense treated SS141 marrow cells. On the right, from right to left are the results of semiquantitative RT-PCR of the common beta sub-unit of the GM-CSF, IL-3 and IL-5 receptors; lane 2 shows the inhibition of gene expression with RB141A. (AS 141). Brown Norway rats were anesthetized with pentothal (65 mg/Kg i.p.). They were then killed, lower extremities retrieved and femurs isolated. The bones were incubated in 70% ethanol for 10 minutes. The two extremities of the bones were sectioned and bone marrow obtained by injection and aspiration of 15 ml of RPMI 1640. The cells were washed twice and incubated for 6 hours in RPMI 1640 at 37° C. in 5% $CO_2$ with medium alone, 10 µM RB141A or 10 µM of the sense oligonucleotide RB141S: 5'-CAGCCACCTA AAGTGCCA-3' (SEQ ID NO:17).

Figure 18A:
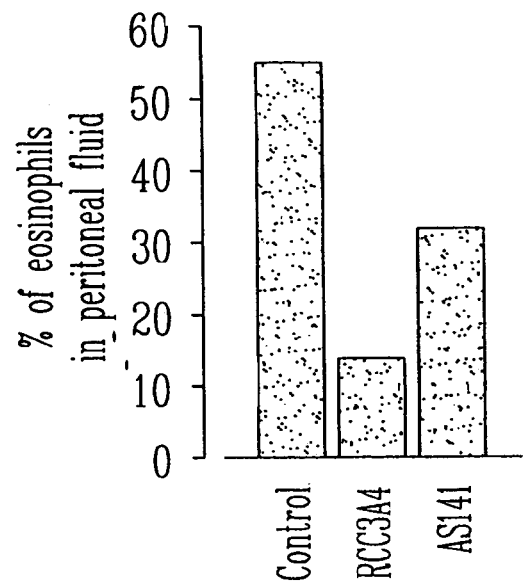
FIGS. 18A and 18B illustrate the antisense phosphorothioate oligonucleotides RB141A (directed against the beta sub-unit of the rat GM-CSF, IL-3 and IL-5 receptors), RCC3A4 (directed against the rat CCR3 receptor) or a combination of both inhibiting eosinophil influx into the peritoneal cavity (left) or the lungs (right) after ovalbumin challenge.
Figure 18B:
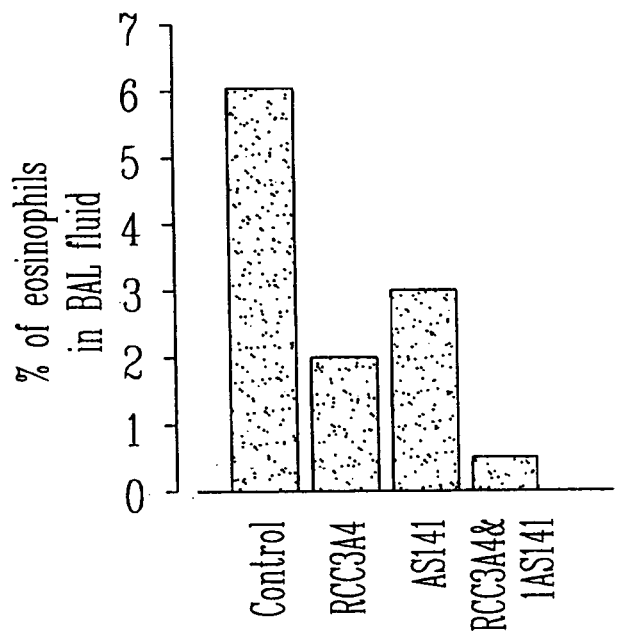

In additional experiments, Brown Norway rats were actively sensitized to ovalbumin by injecting 1.25 mg ovalbumin mixed with 200 mg aluminum hydroxide sub-cutaneously. On day 14, rats received 500 µg of RB141A in 500 µl of 0.9% NaCl intra-peritoneally. The next day, after general anesthesia with 65 mg/Kg pentothal and endotracheal intubation, 200 µg of the antisense is administered either intra-tracheally or intra-peritoneally in 50 µl of 0.9% NaCl. Twenty minutes later ovalbumin challenge is performed by injecting 200 micrograms of ovalbumin in 50 µl either intra-tracheally or intra-peritoneally. After 8 hours, the rats are again intubated after general anesthesia and a lung lavage consisting of 5 times 5 ml instillations or a peritoneal lavage with 8 ml is performed. Cells are washed, counted and centrifuged onto slides in a Cytospin III. A differential cell count is performed. It is to be noted in FIG. A that the antisense oligonucleotide RB141A directed against the common beta chain of the GM-CSF, IL-3 and IL-5 receptors inhibits eosinophil influx into the lungs or the peritoneal cavity by approximately 50%. In FIG. 18A are the results obtained from peritoneal fluid showing the effects of RB141 (AS141). In FIG. 18B are the results from lung BAL showing the effects of RB141 (AS141).

These results show that antisense oligonucleotides directed against the common beta chain of the GM-CSF, IL-3 and IL-5 receptors are important in the prevention of the eosinophil influx and/or survival that occurs in different allergic diseases.

As can be shown from FIGS. 15 to 18, the antisense oligonucleotides of the present invention directed against the common beta sub-unit of the IL-3, IL-5 and GM-CSF receptors are effective at inhibiting receptor expression, cell growth, eosinophil recruitment and survival.

EXAMPLE IV

Antisense Oligonucleotides Inhibiting the CCR3 Receptor for Chemokines

Figure 19:
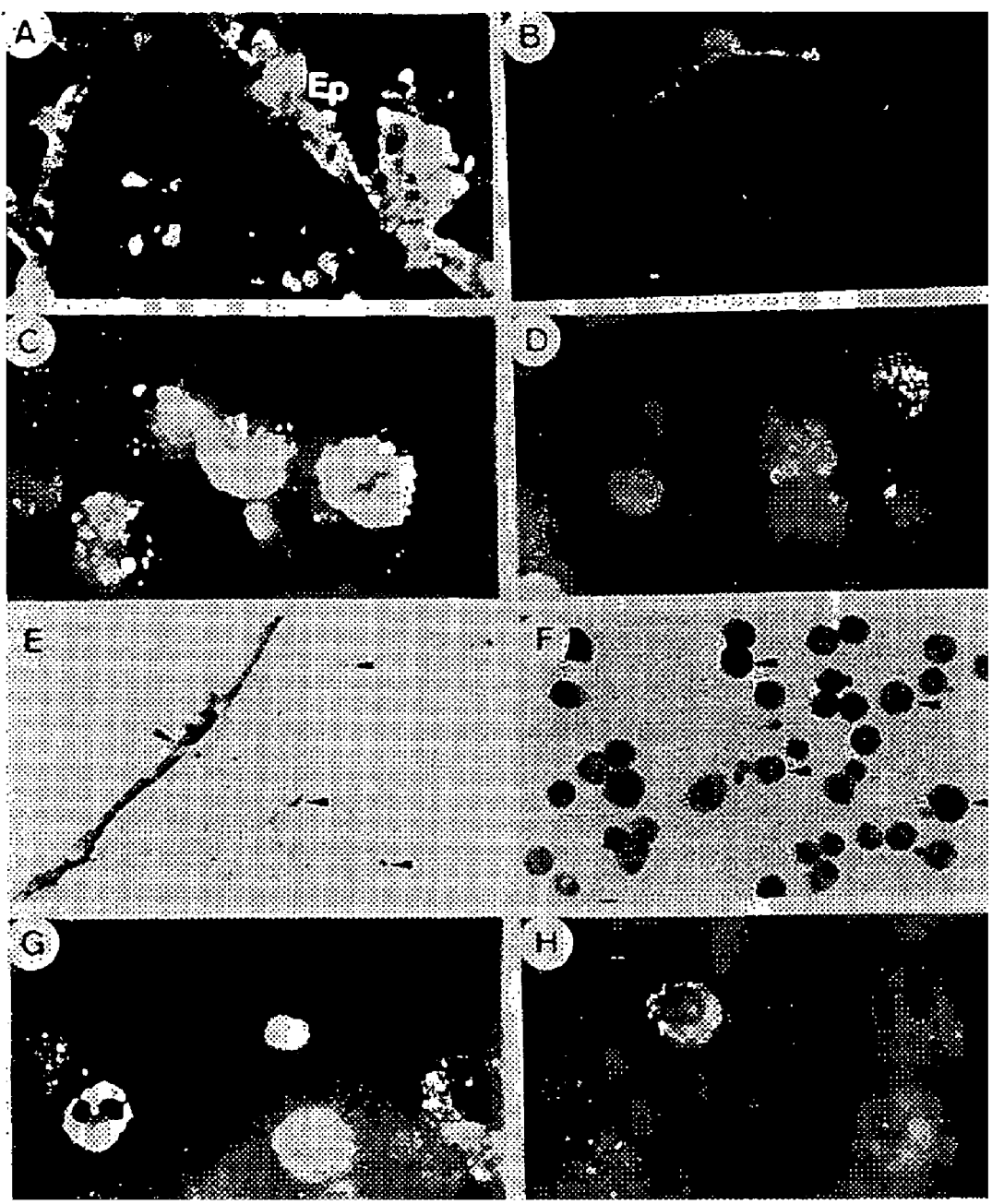
FIGS. 19A to 19H illustrate the expression and cellular distribution of eotaxin mRNA (FIGS. 19A to 19D) and protein (FIGS. 19E to 19H) in airways (FIGS. 19A, 19B, 19E) and BAL cells (FIGS. 19C, 19D, 19F to 19H) of allergic asthmatic patients (FIGS. 19A, 19C, 19E, 19F, 19G) and normal controls (FIGS. 19B, 19D, 19H)

There are two (2) considerations with regards to the CCR3 receptor: 1) it is expressed on the Th2 and not on the Th1 lymphocytes, 2) the CCR3 receptor is important for the recruitment of eosinophils into the sites of allergic or asthmatic inflammation. The chemokines Eotaxin, MCP-4 and RANTES mediate most of their effects through the CCR3 receptor. These chemokines are present and increased in the lungs of patients with allergy and asthma (Lamkhioued et al., Journal of Immunology, 159:4593-4601, 1997). FIG. 19 shows that eotaxin is increased in epithelial cells and inflammatory cells in the lungs of patients with allergy and asthma. The expression and cellular distribution of eotaxin mRNA (19A to 19D) and protein (19E to 19H) in airways (19A, 19B, 19E) and BAL cells (19C, 19D, 19F to 19H) of asthmatic patients and normal controls have been assessed. Eotaxin mRNA expression is increased in asthmatic (19A) compared with normal (19B) airways. Prominent staining is observed in epithelial cells (Ep) and in many inflammatory cells (arrowheads) of the allergic asthmatic airway. FIGS. 19C and 19D are representative examples of in situ hybridization of cytospin preparations of BAL cells obtained from an asthmatic patient and a normal control, respectively. Biopsy cell samples and biopsy sections were hybridized with an FITC-labeled antisense riboprobe complementary to eotaxin mRNA. The majority of positively hybridized cells in the BAL exhibited a morphology consistent with the macrophages (arrowheads). FIG. 19E shows immunohistochemical detection of eotaxin in a representative biopsy section of an asthmatic patient. Eotaxin immunoreactivity was visualized with the fast red chromogen and localized to the epithelial and inflammatory cells (arrowheads). FIG. 19F is a colocalization of eotaxin immunoreactivity (red) to CD-68 positive macrophages (brown) in BAL cells from an asthmatic patient by double immunohistochemistry. Examples of double positive cells are indicated with arrowheads. FIGS. 19G and 19H show eotaxin immunofluorescent staining of BAL cells obtained from an asthmatic patient and a normal control, respectively. Note the eotaxin immunostaining in eosinophils (arrowheads).

The contribution of the different chemokines present in the lungs of allergic patients with asthma to chemotaxis of purified eosinophils has also been assessed. Accordingly, lung bronchoalveolar lavage was performed in asthmatics. The supernatant was concentrated 10-fold with centricon™ columns. The inhibitory effect of antibodies directed against different chemokines on eosinophil migration in response to BAL fluid is assessed in Table 2. BAL fluid was preincubated with buffer, control Abs, polyclonal rabbit anti-eotaxin, anti-MCP-4, anti-RANTES Abs or a combination of these Abs for one hour before the chemotaxis assay was performed. The concentration of the eotaxin used in the BAL in each assay is indicated. Experiments were performed with a 48-well micro-chemotaxis chamber (NeuroProbe). Migration of human eosinophils was performed on a polycarbonate filter (5 µm pore size). Eosinophils ($2 \times 10^6$ cells/ml) were resuspended in RPMI medium, loaded into the chambers, incubated at 37° C., 5% $CO_2$ for 60 min. and the filters were fixed and stained with a RAL kit (Labonord, France). Eosinophils were counted by microscopy in five selected high power fields (magnification×400). For comparison of results from different chemotaxis assay, a chemotactic index (CI) was calculated as follows: CI=(Counts-test sample)/(Counts-control medium). In the formula counts-test sample represents the number of migrated cells toward BAL or eotaxin, counts-control is the mean migration of cells in response to RPMI. The percentage of inhibition of locomotion and the confidence interval are presented for experiments performed on eosinophils obtained from 3 individuals. Percentage of inhibition was calculated by the formula: 100−{(mean no. of migrated cells in Ab-treated fluids)/(mean number of migrated cells in untreated fluid)}×100.

TABLE 2

Inhibitory effect of antibodies (Abs) on eosinophil migration in response to bronchoalveolar lavage (BAL) fluid

| BAL Eotaxin Concentration (pg/ml) | % Inhibition of Migration | | | | | | | |
|---|---|---|---|---|---|---|---|---|
| | BAL/4 | Anti-Eotax[a] | Anti-RANTES[a] | Anti-MCP4[a] | Anti-Eotax + Anti-RANTES[b] | Anti-Eotax + Anti-MCP4[b] | Anti-Eotax + Anti-RANTES + Anti-MCP4[b] | NRS |
| 714.4 | 0 | 21.40 | 15.23 | 13.33 | 25.70 | 30.48 | 37.62 | 0.95 |
| 504.6 | 0 | 29.03 | 10.96 | 12.26 | 36.13 | 34.19 | 57.42 | 4.5 |
| 453.2 | 0 | 32.90 | 18.30 | 15.24 | 43.90 | 35.97 | 53.66 | 4.9 |

[a]$p < 0.05$ for the confidence interval compared with BAL sample alone; and
[b]$p < 0.01$ for the confidence interval compared with BAL sample alone.
NRS: Normal Rabbit Serum In Table 2, the 3 chemokines that act mostly through the CCR3 receptor account for approximately 50% of the chemotaxis of eosinophils in asthmatic BAL.

These results show that chemokines (that act through the CCR3 receptor) are increased and important in allergic asthma and inhibition of the CCR3 receptor with antisense oligonucleotides is thus important in the therapy of allergy and asthma.

Experiments were performed to determine whether antisense oligonucleotides directed against the CCR3 receptor could inhibit the mRNA expression of this receptor. It is to be noted in FIG. 20 that the antisense oligonucleotide directed against the CCR3 receptor, (CCR3AS 86 (RC86A): 5'-CTGGGCCATC AGTGCTCTG-3' SEQ ID NO:18) is effective at inhibiting the expression of mRNA for CCR3 in HL60 cells that have been differentiated into the eosinophil pathway. The housekeeping gene that was used to standardize the mRNA preparation was G3PDH (451 bp band, gel on the right). The gel on the left shows that when compared to the sense oligonucleotide (CCR3SS 86: 5'-CAGAGCACTG ATGGCCCAG-3'; SEQ ID NO:19), RC86A inhibits mRNA for CCR3 (middle lane). HL60 cells (clone 15) were differentiated into eosinophil like cells by incubation for 10 days in RPMI 1640 supplemented with 10% heat-inactivated fetal calf serum, penicillin, streptomycin, 1-glutamine and 0.5 molar acetic acid at 37° C. in 5% $CO_2$ with medium alone, 10 μM CCCR3AS1 or 10 μM CCR3Ss for 6 hours. mRNA was isolated with trizol and after standardization of the amount of mRNA with G3PDH, the expression of mRNA for CCR3 was assessed in mRNA obtained from cells cultured in medium (control), with CCR3AS 86 (middle lane) or with CCR3SS 86 (right lane).

Experiments were also performed to assess whether antisense oligonucleotides directed against the CCR3 receptor could inhibit the mRNA expression of this receptor on Ghost cells transfected with the CCR3 receptor. These cells were obtained from the NIH and the CCR3 gene was introduced via retroviral infection with MLV BABE-puro vector. It is to be noted in FIG. 21, gel on the right, that the antisense oligonucleotide directed against the CCR3 receptor (RC86A) is effective at inhibiting mRNA expression of the CCR3 receptor when compared to control not incubated with 10 μMol antisense. The gel on the left shows the results obtained for the housekeeping gene G3PDH.

Additional experiments were performed to assess whether antisense oligonucleotides directed against the CCR3 receptor could inhibit the function of this receptor. It is to be noted in FIG. 22 that the antisense oligonucleotide directed against the CCR3 receptor (RC269AS: 5'-CCCTGACATA GTG-GATC-3' SEQ ID NO:20 ) and RC86A are effective at inhibiting calcium mobilization (a sign of chemotaxis) in eosinophils. Human eosinophils were purified from blood obtained from patients with asthma by Ficoll Hypaque centrifugation, red blood cell lysis, followed by negative selection with anti-CD16 coated magnetic beads on a MACS cell sorter (to eliminate neutrophils). The eosinophils were then washed and incubated with recombinant human IL-5 (1.6 ng/ml) in RPMI 1640 supplemented with 10% heat-inactivated fetal calf serum, penicillin, streptomycin, and 1-glutamine at 37° C. in 5% $CO_2$ overnight. The cells were washed and then incubated in RPMI 1640 during 4 hours in the presence or absence of 10 μM RC269AS or 10 μM RC269S 5'-GATC-CACTAT GTCAGGG-3' (SEQ ID NO:21) washed and resuspended at 2.5×106 cells/ml in RPMI 1640 and incubated with Fura-2M at a concentration of 3 μM for 45 minutes. Thq cells were washed twice with PBS and resuspended in calcium buffer (PBS, 1 mM HEPES, 1 mM Ca++). Calcium efflux after immediate stimulation with eotaxin was measured with a Perkin Elmer L50B Spectrophotometer (excitation at 340 nm, slit 5 nm and emission at 492 nm, slit 5 nm).

Figure 23:
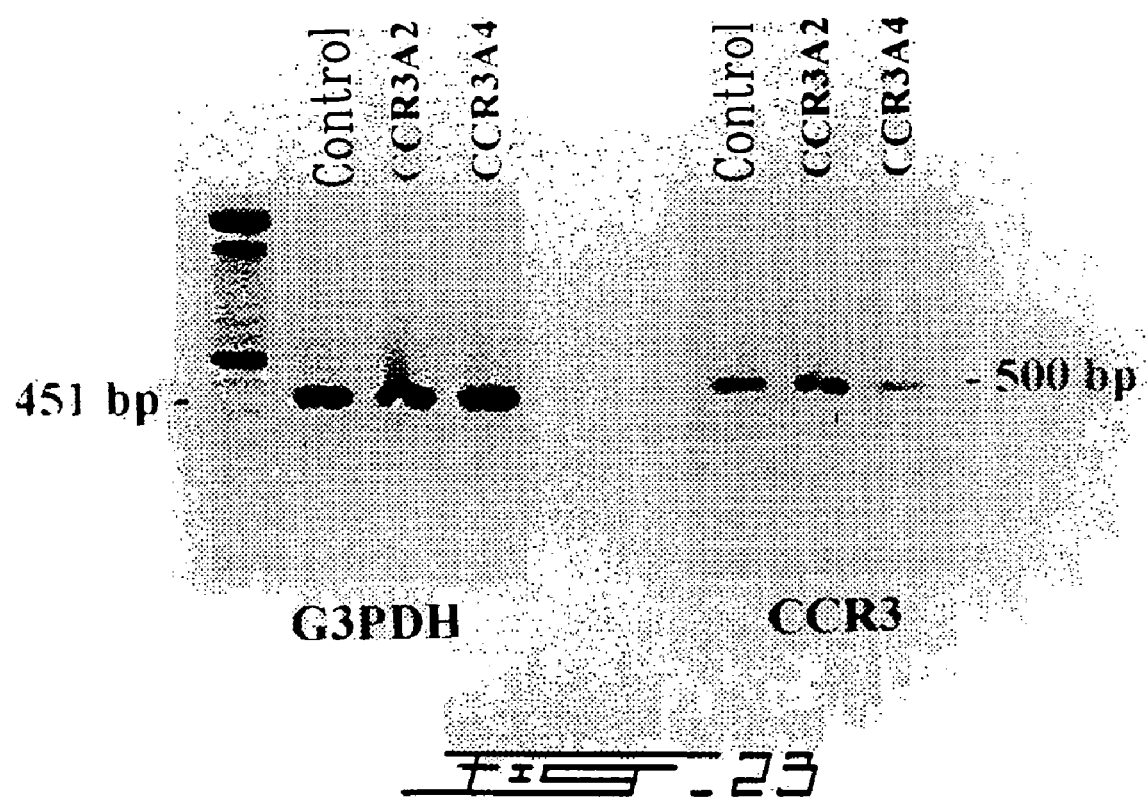
FIG. 23 illustrates the effect of the phosphorothioate antisense oligonucleotide RCC3A4 directed against the rat CCR3 receptor on CCR3 mRNA expression in rat bone marrow cells.

Experiments were then performed to determine whether antisense oligonucleotides directed against the CCR3 receptor could inhibit the influx of eosinophils in vivo. It is to be noted in FIG. 23 that the phosphorothioate antisense oligonucleotide RCC3A4 5'-ACTCATATTC ATAGGGTG-3' (SEQ ID NO:22) is effective at inhibiting mRNA expression of rat CCR3 in vitro. On the left are results of semi-quantitative RT-PCR for the G3PDH gene in control medium without antisense, in medium with CCR3A2 (5'-GCCAACACAG CATGAACG-3', SEQ ID NO:23) an antisense that has proven to be ineffective against CCR3 receptor expression and in medium with RCC3A4 (10 μMol) treated marrow cells. On the right, from right to left are the results of semi-quantitative RT-PCR of the rat CCR3 receptor; lane 1 shows the inhibition of gene expression with RCC3A4. Brown Norway rats were anesthetized with pentothal (65 mg/Kg i.p.). They were then killed, lower extremities retrieved and femurs isolated. The bones were incubated in 70% ethanol for 10 minutes. The two extremities of the bones were sectioned and bone marrow obtained by injection and aspiration of 15 ml of RPMI 1640. The cells were washed twice and incubated for 6 hours in RPMI 1640 at 37° C. in 5% $CO_2$ with medium alone, medium with 10 μM of RC3A2 or with 10 μM RCC3A4.

Additional experiments show that antisense oligonucleotides directed against the CCR3 receptor are effective at inhibiting eosinophil influx into the peritoneal cavity and into the lungs in vivo. Brown Norway rats were actively sensitized to ovalbumin by injecting 1.25 mg ovalbumin mixed with 200 mg aluminum hydroxide sub-cutaneously. On day 14, rats received 500 micrograms of RCC3A4 in 500 μl of 0.9% NaCl or 0.9% NaCl intra-peritoneally. The next day the rats were challenged by administering 1.25 mg of ovalbumin intra-peritoneally. Eight hours later the rats are anesthetized with 65 mg/Kg of pentothal, the abdominal cavity opened and washed with 8 ml of RPMI 1640. The washing solution is retrieved, cells are washed, counted and centrifuged onto slides in a Cytospin III. A differential cell count is performed. It is to be noted in FIG. 18A that the antisense oligonucleotide RCC3A4 directed against the CCR3 receptor inhibits eosinophil influx into the peritoneal cavity by approximately 60%.

In additional experiments Brown Norway rats were actively sensitized to ovalbumin by injecting 1.25 mg ovalbumin mixed with 200 mg aluminum hydroxide subcutaneously. On day 14, rats received 500 µg of RCC3A4 in 500 µl of 0.9% NaCl or 0.9% NaCl intra-peritoneally. The next day, after general anesthesia with 65 mg/Kg pentothal and endotracheal intubation, 200 µg of the antisense is administered intra-tracheally in 50 µl of 0.9% NaCl. Twenty minutes later ovalbumin challenge is performed by injecting 200 micrograms of ovalbumin in 50 µl intra-tracheally. After 8 hours, the rats are again intubated after general anesthesia and a lung lavage consisting of 5 times 5 ml installations is performed. Cells are washed, counted and centrifuged onto slides in a Cytospin III. A differential cell count is performed. It is to be noted in FIG. 18B hat the antisense oligonucleotide RCC3A4 directed against the CCR3 receptor inhibits eosinophil influx into the lungs by approximately 66%.

These results show that antisense oligonucleotides directed against the CCR3 receptor are important in the prevention of the eosinophil influx that occurs in different allergic diseases and thus their effects.

Furthermore, priming with the cytokine IL-5 (which acts through the IL-5 receptor) can either increase the chemotaxis of cells or the release of chemokines when the cells are stimulated.

Figure 24:
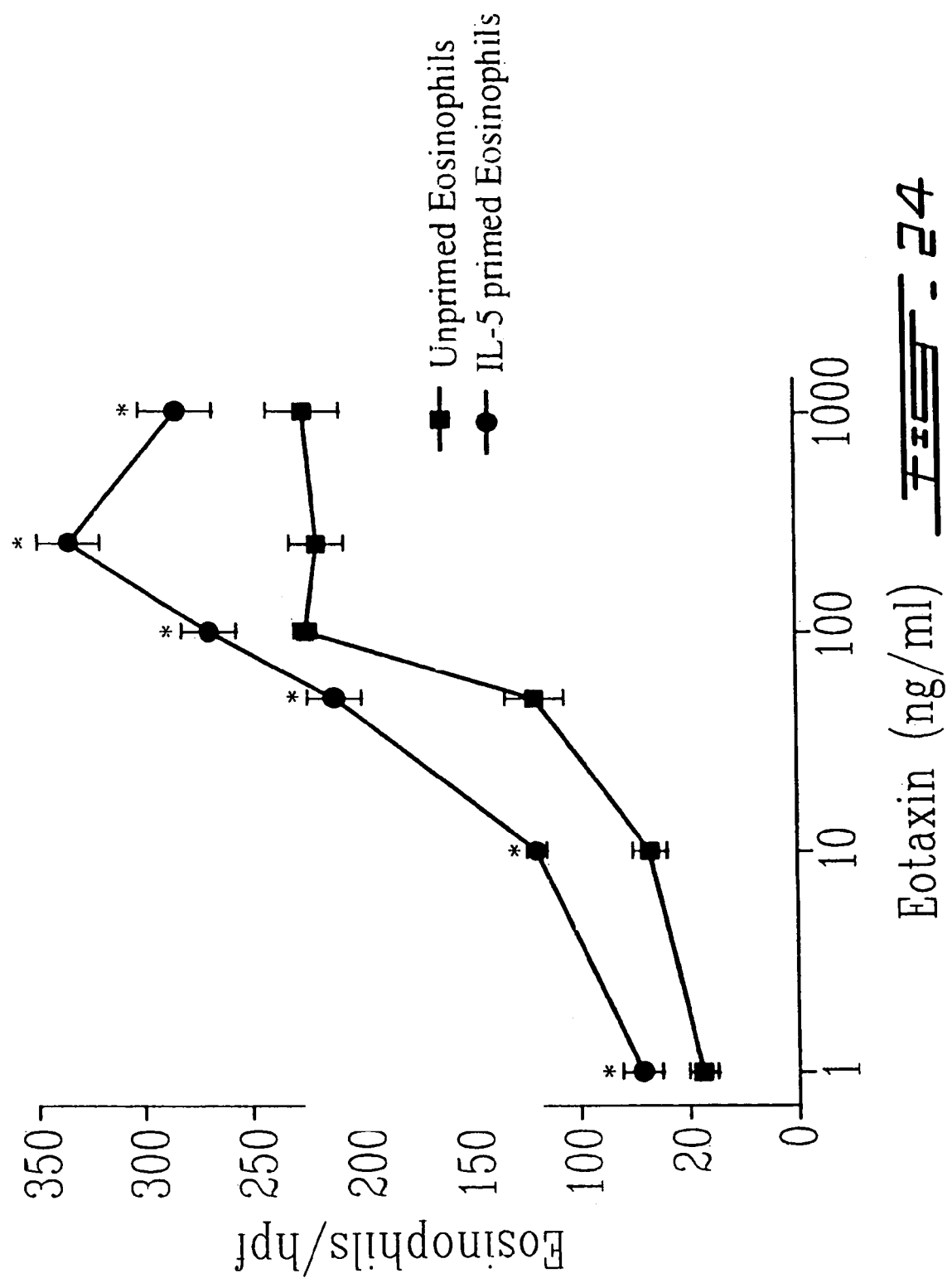
FIG. 24 illustrates the effect of preincubation with IL-5 on the chemotaxis induced by eotaxin.

FIG. 24 shows that priming of eosinophils with IL-5 increases the chemotaxis of eosinophils when they are stimulated with eotaxin. Preincubation of eosinophils with IL-5 (which acts through the IL-5 receptor) increases the chemotaxis induced by eotaxin at every dose tested. The peak of chemotaxis is higher with priming which suggests a synergistic effect of IL-5 on the effects of eotaxin. Dose-response curves show the chemotactic activity of purified human eosinophils to eotaxin (filled squares) and transmigration through a polycarbonate filter after preincubation with IL-5 (closed circles). Mononuclear cells and granulocytes were purified from peripheral blood by Ficoll-Paque (Pharmacia) density centrifugation. Granulocytes were obtained by dextran sedimentation. Human eosinophils were further purified by negative selection with anti-CD16 and anti-CD3-coated immunomagnetic microbeads using a Magnetic Cell Sorting System (Miltenyi Biotec) at 4° C. The degree of purity of eosinophil populations, estimated after staining with Giemsa, was between 92 and 100%. Results are presented as mean±SD of 5 high power fields. Control serum had no effect on chemotaxis. Results identified by "*" represent a probability of being different of p<0.01 compared with unprimed eosinophils at each concentration of eotaxin.

Figure 25:
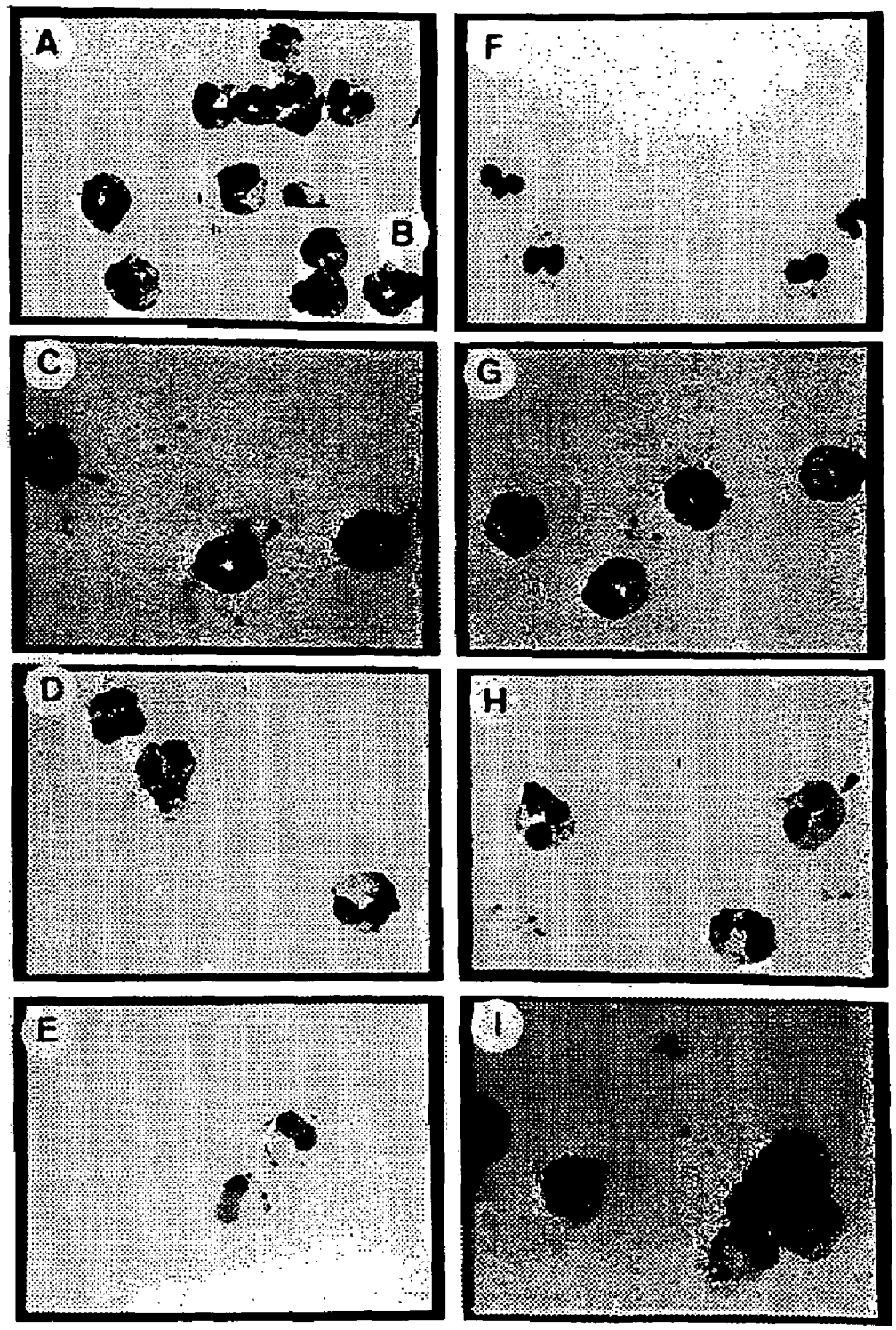
FIGS. 25A to 25I illustrate the effect of preincubation with IL-5 overnight on chemokine production.

FIGS. 25a to 25I show that priming of eosinophils with IL-5 increases the amount of chemokines in the cells and increases their release after stimulation with immunoglobulin. Preincubation of eosinophils with IL-5 overnight increased the expression of eotaxin (FIG. 25A) and MCP-4 (FIG. 25B) when compared to controls (FIG. 25F). When eosinophils are stimulated with IgE-anti-IgE they will also release eotaxin (FIGS. 25C, 25D, 25E) or MCP-4 (FIGS. 25G, 25H, 25I). Eosinophils were purified as described above and incubated overnight with recombinant human IL-5 (1 ng/ml). This incubation increased eotaxin (FIG. 25A) and MCP-4 (FIG. 25B) in cells when compared to control cells incubated in medium alone (FIG. 25F). Stimulation of the eosinophils by a preincubation with IgE for 15 minutes then exposure to anti-IgE lead to a progressive release eotaxin (FIGS. 25C, 25D, 25E) or MCP-4 (FIGS. 25G, 25H, 25I) at 15 minutes (FIGS. 25C, 25G), 2 hours (FIGS. 25D, 25H) or 12 hours (FIGS. 25E, 25I).

Accordingly, the combination of antisense oligonucleotides in accordance with the present invention, that are directed against different receptors (for example the IL-5 and the CCR3 receptors) have a synergistic effect in the therapy of allergy, asthma or neoplastic cell proliferation.

Experiments were performed in Brown Norway rats in order to assess whether the combination of the antisense phosphorothioate RB141A directed against the common beta chain of the. GM-CSF, IL-3 and IL-5 receptors and the antisense phosphorothioate RCC3A4 directed against the CCR3 receptor had synergistic effects on eosinophil recruitment into the lungs after antigen challenge when compared to either one alone. Brown Norway rats were actively sensitized to ovalbumin by injecting 1.25 mg ovalbumin mixed with 200 mg aluminum hydroxide sub-cutaneously. On day 14, rats received 500 µg of RCC3A4 and 500 µg of RB141A in 500 µl of 0.9% NaCl or 0.9% NaCl intra-peritoneally. The next day, after general anesthesia with 65 mg/Kg pentothal and endotracheal intubation, 180 µg of each antisense is administered intra-tracheally in 60 µl of 0.9% NaCl. Twenty minutes later ovalbumin challenge is performed by injecting 200 micrograms of ovalbumin in 60 µl intra-tracheally. After 8 hours, the rats are again intubated after general anesthesia and a lung lavage consisting of 5 times 5 ml installations is performed. Cells are washed, counted and centrifuged onto slides in a Cytospin III. A differential cell count is performed. It is to be noted in FIG. 18B that the combination of antisense oligonucleotide RCC3A4 and RB141A directed against the CCR3 receptor and common beta sub-unit of the GM-CSF, IL-3 and IL-5 receptors have a synergistic effect on eosinophil influx into the lungs. The inhibition of eosinophil influx was approximately 90%.

The antisense oligonucleotides of the present invention when compared to the use of soluble IL-4 receptors in allergy and asthma has the following advantages: a) as shown in example 1, the much smaller size of these molecules permits them to diffuse into the tissues and penetrate the cells that are expressing the receptors (epithelial cells, smooth muscle cells); b) the use of an antisense oligonucleotide against the common sub-unit of the IL-4 and IL-13 receptor permits a broader effect by blocking the effects of IL-13 that are similar to those of IL-4 in many respects on IgE production, as IL-13 is also increased in allergy and asthma; and c) the combination of anti-receptor oligonucleotides against receptors for many cytokines (IL-3, IL-5 and GM-CSF or IL-4 and IL-13 or CCR3 (eotaxin, RANTES and MCP-4)) will permit broader effects in a disease where a certain individual's heterogeneity in the inflammatory cascade exist.

Furthermore, the antisense oligonucleotides of the present invention have the following advantages: a) the antisense anti-receptor oligonucleotides will act directly on tissue or inflammatory cells that are present at the site of administration and not indirectly by potentially blocking the release of mediators (if directed against the cytokines themselves); b) the antisense anti-receptor oligonucleotides will not be affected by diffusion of cytokines that are produced and increased in the blood is of patients with allergy and asthma;

and c) one antisense anti-receptor oligonucleotide of the present invention blocks the effects of 2 or 3 mediators which have been shown to be increased in allergy or asthma, thus having a broader effect than one antisense oligonucleotide directed only against one mediator or receptor and therefore being an advantage.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

The invention claimed is:

1. A pharmaceutical composition comprising an oligonucleotide having a base sequence consisting of SEQ ID NO:9.

2. A pharmaceutical composition for treating asthma or allergy said composition comprising an oligonucleotide having a base sequence consisting of SEQ ID NO:9 in association with a pharmaceutically acceptable carrier.

3. The pharmaceutical composition of claim 2, further comprising at least one oligonucleotide directed against a nucleic acid encoding a Chemokine (C-C motif) receptor 3 (CCR3).

4. The pharmaceutical composition according to claim 3, wherein the at least one oligonucleotide with SEQ ID NO: 18 is directed against a nucleic acid encoding a Chemokine (C-C motif) receptor 3 (CCR3).

5. An oligonucleotide having a base sequence consisting of SEQ ID NO:9 and comprising at least one phosphorothioate internucleotide linkage.

6. The oligonucleotide of claim 5, comprising all phosphorothioate internucleotide linkages.

7. The oligonucleotide of claim 1, comprising at least one phosphodiester internucleotide linkage.

8. The oligonucleotide of claim 7, comprising all phosphodiester internucleotide linkages.

9. A pharmaceutical composition for treating asthma or allergy said composition comprising an oligonucleotide having a base sequence consisting of SEQ ID NO:9 and comprising at least one phosphorothioate internucleotide linkage, in association with a pharmaceutically acceptable carrier.

10. A pharmaceutical composition for treating asthma or allergy said composition comprising the oligonucleotide as defined in claim 6, in association with a pharmaceutically acceptable carrier.

11. A pharmaceutical composition for treating asthma or allergy said composition comprising the oligonucleotide as defined in claim 7, in association with a pharmaceutically acceptable carrier.

12. A pharmaceutical composition for treating asthma or allergy said composition comprising the oligonucleotide as defined in claim 8, in association with a pharmaceutically acceptable carrier.

* * * * *

UNITED STATES PATENT AND TRADEMARK OFFICE
CERTIFICATE OF CORRECTION

PATENT NO. : 7,629,324 B2  Page 1 of 1
APPLICATION NO. : 10/958204
DATED : December 8, 2009
INVENTOR(S) : Paolo Renzi It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 981 days.

Signed and Sealed this

Second Day of November, 2010

David J. Kappos
*Director of the United States Patent and Trademark Office*